US009596989B2

(12) United States Patent
Morris

(10) Patent No.: US 9,596,989 B2
(45) Date of Patent: Mar. 21, 2017

(54) NETWORKED SYMBIOTIC EDGE USER INFRASTRUCTURE

(75) Inventor: Timothy R. Morris, Fort Wayne, IN (US)

(73) Assignee: Raytheon Company, Waltham, MA (US)

( * ) Notice: Subject to any disclaimer, the term of this patent is extended or adjusted under 35 U.S.C. 154(b) by 346 days.

(21) Appl. No.: 12/713,216

(22) Filed: Feb. 26, 2010

(65) Prior Publication Data

US 2010/0234695 A1 Sep. 16, 2010

Related U.S. Application Data

(60) Provisional application No. 61/159,600, filed on Mar. 12, 2009.

(51) Int. Cl.
*A61B 5/00* (2006.01)
*H04W 4/00* (2009.01)
*H04W 84/00* (2009.01)
*G06F 19/00* (2011.01)
*H04W 84/18* (2009.01)
(Continued)

(52) U.S. Cl.
CPC .......... *A61B 5/0002* (2013.01); *A61B 5/0024* (2013.01); *A61B 5/681* (2013.01); *G06F 19/3418* (2013.01); *G06Q 50/24* (2013.01); *H04M 11/002* (2013.01);
(Continued)

(58) Field of Classification Search
USPC .................................................. 600/300–301
See application file for complete search history.

(56) References Cited

U.S. PATENT DOCUMENTS 5,451,839 A 9/1995 Rappaport et al.
5,936,539 A 8/1999 Fuchs
(Continued)

FOREIGN PATENT DOCUMENTS

CA 2 644 695 1/2004
CA 2 648 885 11/2007
(Continued)

OTHER PUBLICATIONS

Microvision, Inc., Product literature for Microvision Wearable Displays, available at www.microvision.com, copyright 1996-2009, 5 pages.
(Continued)

*Primary Examiner* — William Thomson
*Assistant Examiner* — Marie Archer
(74) *Attorney, Agent, or Firm* — Daly, Crowley, Mofford & Durkee, LLP

(57) ABSTRACT

A networked symbiotic assistive user system is presented. The architecture of the system allows devices worn by medical first responders such as medics or EMTs, to connect wirelessly to devices coupled to patients, devices worn by other medical first responders and adapter devices (such as those that may be located in air and/or land evacuation vehicles) that connect to a legacy infrastructure. Using a variety of medical first responder oriented communications protocols and applications, the devices can exchange information with all of the other devices in a manner that assists the medical first responders as well as personnel associated with the legacy infrastructure (e.g., tactical command operations personnel, first aid station personnel, or other medical facilities personnel).

19 Claims, 13 Drawing Sheets

(51) Int. Cl.
*G06Q 50/24* (2012.01)
*H04M 11/00* (2006.01)

(52) U.S. Cl.
CPC ......... *H04W 4/008* (2013.01); *H04W 84/005* (2013.01); *H04W 84/18* (2013.01); *A61B 5/742* (2013.01)

(56) References Cited

U.S. PATENT DOCUMENTS

| | | |
|---|---|---|
| 6,221,012 B1 | 4/2001 | Maschke et al. |
| 6,377,162 B1 | 4/2002 | Delestienne et al. |
| 6,377,806 B1 | 4/2002 | Tokuyoshi |
| 6,442,433 B1 | 8/2002 | Linberg |
| 6,519,569 B1 | 2/2003 | White et al. |
| 6,578,002 B1 | 6/2003 | Derzay et al. |
| 6,790,198 B1 | 9/2004 | White et al. |
| 6,839,753 B2 | 1/2005 | Biondi et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,512,889 B2 | 3/2009 | Newell et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,605,714 B2 | 10/2009 | Thompson et al. |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,937,370 B2 | 5/2011 | Hansen |
| 7,942,844 B2 | 5/2011 | Moberg et al. |
| 7,949,404 B2 | 5/2011 | Hill |
| 7,965,178 B1* | 6/2011 | Schmuttor et al. ............ 340/506 |
| 7,978,062 B2* | 7/2011 | LaLonde et al. ........ 340/539.11 |
| 8,002,701 B2 | 8/2011 | John et al. |
| RE42,934 E | 11/2011 | Thompson |
| 8,073,008 B2 | 12/2011 | Mehta et al. |
| 8,095,381 B2 | 1/2012 | Simmons et al. |
| 8,108,543 B2 | 1/2012 | Hansen |
| 8,125,318 B2 | 2/2012 | Heimbrock et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,200,195 B2 | 6/2012 | Le Saint et al. |
| 8,214,549 B2 | 7/2012 | Dicks et al. |
| 8,326,648 B2 | 12/2012 | Kenedy et al. |
| 8,373,556 B2 | 2/2013 | LaLonde et al. |
| 8,395,498 B2 | 3/2013 | Gaskill et al. |
| 8,428,722 B2 | 4/2013 | Verhoef et al. |
| 8,515,547 B2 | 8/2013 | Mass et al. |
| 8,587,427 B2 | 11/2013 | LaLonde et al. |
| 8,694,600 B2 | 4/2014 | Gaines et al. |
| 2002/0178126 A1 | 11/2002 | Beck et al. |
| 2002/0198473 A1 | 12/2002 | Kumar et al. |
| 2004/0034284 A1* | 2/2004 | Aversano et al. ............. 600/300 |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0110640 A1* | 5/2005 | Chung ............... G06K 7/10346 340/572.1 |
| 2005/0185398 A1 | 8/2005 | Scannell, Jr. |
| 2005/0188853 A1 | 9/2005 | Scannell, Jr. |
| 2005/0201300 A1 | 9/2005 | Bridgelall |
| 2005/0206518 A1* | 9/2005 | Welch et al. ............ 340/539.12 |
| 2005/0234308 A1* | 10/2005 | Naukkarinen ................ 600/300 |
| 2005/0243988 A1 | 11/2005 | Barclay et al. |
| 2005/0288571 A1 | 12/2005 | Perkins et al. |
| 2006/0066449 A1* | 3/2006 | Johnson .................... 340/539.12 |
| 2006/0121846 A1* | 6/2006 | Mazar et al. ..................... 455/7 |
| 2006/0154642 A1 | 7/2006 | Scannell, Jr. |
| 2006/0202816 A1* | 9/2006 | Crump ............... A61B 5/02055 340/539.12 |
| 2006/0224048 A1* | 10/2006 | Devaul et al. ................. 600/300 |
| 2006/0238333 A1 | 10/2006 | Welch et al. |
| 2006/0252999 A1* | 11/2006 | Devaul et al. ................. 600/300 |
| 2007/0106126 A1 | 5/2007 | Mannheimer et al. |
| 2007/0135866 A1* | 6/2007 | Baker et al. ..................... 607/60 |
| 2007/0156033 A1 | 7/2007 | Causey, III et al. |
| 2007/0180140 A1* | 8/2007 | Welch et al. .................. 709/238 |
| 2007/0186923 A1 | 8/2007 | Poutiatine et al. |
| 2007/0216764 A1 | 9/2007 | Kwak |
| 2007/0230197 A1 | 10/2007 | Scannell, Jr. |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255250 A1 | 11/2007 | Moberg et al. |
| 2007/0257788 A1* | 11/2007 | Carlson et al. ................ 340/506 |
| 2007/0258395 A1 | 11/2007 | Jollota et al. |
| 2007/0268687 A1 | 11/2007 | Scannell, Jr. |
| 2007/0276270 A1 | 11/2007 | Tran |
| 2007/0299480 A1* | 12/2007 | Hill ................................ 607/28 |
| 2008/0001735 A1* | 1/2008 | Tran ........................ 340/539.22 |
| 2008/0004904 A1* | 1/2008 | Tran ................................. 705/2 |
| 2008/0004907 A1 | 1/2008 | Bayne |
| 2008/0012761 A1 | 1/2008 | Derrick et al. |
| 2008/0024294 A1* | 1/2008 | Mazar ...................... 340/539.12 |
| 2008/0071234 A1 | 3/2008 | Kelch et al. |
| 2008/0088436 A1* | 4/2008 | Reeves et al. ........... 340/539.12 |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0103370 A1* | 5/2008 | Dicks et al. .................. 600/300 |
| 2008/0108880 A1 | 5/2008 | Young et al. |
| 2008/0139890 A1* | 6/2008 | Craine et al. ................. 600/300 |
| 2008/0146277 A1* | 6/2008 | Anglin et al. ............... 455/556.1 |
| 2008/0146890 A1* | 6/2008 | LeBoeuf et al. .............. 600/300 |
| 2008/0183502 A1 | 7/2008 | Dicks et al. |
| 2008/0224852 A1 | 9/2008 | Dicks et al. |
| 2008/0228045 A1* | 9/2008 | Gao et al. ..................... 600/301 |
| 2008/0281168 A1 | 11/2008 | Gibson et al. |
| 2008/0294020 A1* | 11/2008 | Sapounas ..................... 600/301 |
| 2009/0019061 A1 | 1/2009 | Scannell, Jr. |
| 2009/0023391 A1 | 1/2009 | Falck |
| 2009/0036750 A1* | 2/2009 | Weinstein et al. ............ 600/300 |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0069642 A1* | 3/2009 | Gao et al. ..................... 600/300 |
| 2009/0073694 A1 | 3/2009 | Scannell, Jr. |
| 2009/0105549 A1 | 4/2009 | Smith et al. |
| 2009/0115628 A1 | 5/2009 | Dicks et al. |
| 2009/0128320 A1 | 5/2009 | Needham et al. |

(56) References Cited

U.S. PATENT DOCUMENTS

| | | |
|---|---|---|
| 2009/0131759 A1* | 5/2009 | Sims et al. ............... 600/301 |
| 2009/0140851 A1* | 6/2009 | Graves et al. .......... 340/539.12 |
| 2009/0149722 A1* | 6/2009 | Abolfathi et al. ............ 600/301 |
| 2009/0174547 A1* | 7/2009 | Greene ................. A62B 99/00 340/539.13 |
| 2009/0184835 A1 | 7/2009 | Deaver, Sr. et al. |
| 2009/0203329 A1 | 8/2009 | White et al. |
| 2009/0231124 A1* | 9/2009 | Klabunde et al. ....... 340/539.12 |
| 2009/0234672 A1 | 9/2009 | Dicks et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2009/0306747 A1 | 12/2009 | Fischer et al. |
| 2009/0326339 A1* | 12/2009 | Horvitz ........................ 600/301 |
| 2010/0011000 A1 | 1/2010 | Chakara et al. |
| 2010/0027518 A1 | 2/2010 | Wang |
| 2010/0077115 A1 | 3/2010 | Rofougran |
| 2010/0079276 A1 | 4/2010 | Collins et al. |
| 2010/0080200 A1 | 4/2010 | Stewart |
| 2010/0082371 A1 | 4/2010 | Kamp et al. |
| 2010/0085948 A1 | 4/2010 | Yu et al. |
| 2010/0094098 A1* | 4/2010 | Smith et al. ................. 600/300 |
| 2010/0117835 A1 | 5/2010 | Nanikashvill |
| 2010/0138235 A1 | 6/2010 | Marks et al. |
| 2010/0166170 A1 | 7/2010 | East et al. |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0222645 A1* | 9/2010 | Nadler et al. ................ 600/300 |
| 2010/0234695 A1 | 9/2010 | Morris |
| 2010/0260061 A1 | 10/2010 | Bojahra et al. |
| 2010/0279647 A1 | 11/2010 | Jacobs et al. |
| 2010/0292556 A1 | 11/2010 | Golden |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1 | 6/2011 | Eaton et al. |
| 2011/0158430 A1 | 6/2011 | Dicks et al. |
| 2011/0161111 A1 | 6/2011 | Dicks et al. |
| 2011/0179405 A1 | 7/2011 | Dicks et al. |
| 2011/0255454 A1 | 10/2011 | Hauser et al. |
| 2011/0270045 A1 | 11/2011 | Lebel et al. |
| 2011/0273287 A1 | 11/2011 | LaLonde et al. |
| 2011/0280224 A1 | 11/2011 | Falck et al. |
| 2011/0282671 A1 | 11/2011 | Dicks et al. |
| 2011/0292862 A1 | 12/2011 | Shimizu |
| 2012/0004925 A1 | 1/2012 | Braverman et al. |
| 2012/0108917 A1 | 5/2012 | Libbus et al. |
| 2012/0182143 A1 | 7/2012 | Gaines et al. |
| 2012/0182894 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0066644 A1 | 3/2013 | Dicks et al. |
| 2013/0147622 A1 | 6/2013 | LaLonde et al. |
| 2013/0154851 A1 | 6/2013 | Gaskill et al. |
| 2013/0162426 A1 | 6/2013 | Wiesner et al. |
| 2013/0278414 A1 | 10/2013 | Sprigg et al. |
| 2013/0310896 A1 | 11/2013 | Mass |
| 2014/0009271 A1 | 1/2014 | Collins et al. |
| 2014/0062718 A1 | 3/2014 | LaLonde et al. |
| 2014/0142979 A1 | 5/2014 | Mitsunaga |
| 2014/0152466 A1 | 6/2014 | Wiesner et al. |

FOREIGN PATENT DOCUMENTS

| | | |
|---|---|---|
| CA | 2 644 635 | 8/2008 |
| CN | 101601040 A | 12/2009 |
| EP | 2 227 063 | 9/2010 |
| JP | 2003-109160 | 4/2003 |
| JP | 2006-520657 | 9/2006 |
| JP | 2007-531442 | 11/2007 |
| JP | 2008-108170 | 5/2008 |
| JP | 2009-535715 A | 1/2009 |
| JP | 2010-524050 A | 7/2010 |
| JP | 2011-502369 A | 1/2011 |
| KR | 10-2008-0016458 | 2/2008 |
| KR | 10-2009-0122968 | 12/2009 |
| KR | 10-2010-0028318 | 3/2010 |
| WO | WO 94/166117 | 8/1994 |
| WO | WO 98/14228 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2005/057294 A1 | 6/2005 |
| WO | WO 2005/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2008/052034 A1 | 5/2008 |
| WO | WO 2008/097316 A1 | 8/2008 |
| WO | WO 2009/032134 A2 | 3/2009 |
| WO | WO 2009/063303 A1 | 5/2009 |
| WO | WO 2010/085138 A2 | 7/2010 |

OTHER PUBLICATIONS

Eurotech Group, Zypad WR11xx—Rugged Wearable Computer, Product Announcement, available at http://www.zypad.com/zypad/news.aspx?pg=news&id=99, Nov. 17, 2008, 1 page.
Eurotech Group, Zypad WL1000 datasheet, available at http://www.eurotech.com/downloadarea/Datasheets/Wearable%20Computers/Zypad%20WL%201000_sf.pdf, undated, 2 pages.
Eurotech Group, Zypad WR11XX data sheet, available at http://www.eurotech.com/downloadarea/Datasheets/Wearable%20Computers/Zypad%20WR1100_sf.pdf, undated, 4 pages.
Eurotech Group, Zypad WL1100 data sheet, available at http://www.eurotech.com/downloadarea/Datasheets/Wearable%20Computers/Zypad%20WL%201100_sf.pdf, possibly dated Sep. 9, 2008, 2 pages.
Corventis, Inc., Product literature—Wireless cardiovascular solutions for continuous patient surveillance, available at http://corventis.com/US/medprof.asp, copyright 2009, 1 page.
Corventis, Inc., Product literature for Nuvant Mobile Cardiac Telemetry (MCT) System, available at http://corventis.com/US/nuvant.asp, copyright 2009, 2 pages.
Corventis, Inc., Product literature for Avivo Mobile Patient Management (MPM) System, available at http://corventis.com/US/avivo.asp, copyright 2009, 2 pages.
Batcheldor; Hospital Tries ZigBee to Track Patients; Jul. 21, 2006.
Bel Air; Capacity of Wireless Mesh Networks; Jun. 28, 1905.
Bogia; Enabling the Future of u-Health-IEEE 11073 Personal Health Devide Standards; Sep. 16, 2009.
Craig; ZigBee Networks; Apr. 1, 2005.
Craig; ZigBee: Wireless Control that Simply Works; Jan. 1, 2011.
Digi Int'l; ConnectPort® X4 H; 2008-2010.
Digi Int'l; Demystifying 802.15.4 and ZigBee®; 2008-2010.
Digi Int'l; Xbee® & Xbee-Pro® ZB; 2008-2010.
Devorak; Remote Monitoring; Apr. 1, 2005.

(56) References Cited

OTHER PUBLICATIONS

EPN Newswire; Freescale Products Achieve ZigBee Health Care Certification; May 19, 2010.
Huang; Medical Electronics: From Hospital and Clinic to the Home; Dec. 5, 2010.
ICPDAS; ZigBee Converter User's Manual; Sep. 22, 2008.
Kawai; Proposal of an Assured Corridor Mechanism for Urgent Information Transmission in Wireless Sensor Networks; Oct. 1, 2007.
Le; Designing a Zig-Bee-Ready IEEE 802.15.4-Compliant Radio Transceiver; Nov. 1, 2004.
Miche; The Internet of Vehicles of the Second Generation of Telematic Services; Apr. 2, 2009.
Norris; Single-Chip ZigBee for Indoor Mobile Telemetry; Jun. 21, 2005.
Pinto; WMM—Wireless Mesh Monitoring; Jul. 1, 1905.
Sallhan; Wireless Mesh Network Monitoring: Design, Implementation and Experiments; Jun. 29, 1905.
Silicon Horizon; TechFX ZigBee Tools v1.0; 2007-2008.
Skibniewski; Utiquitous Computing: Object Tracking and Monitoring in Construction Processing Utilizing Zigbee™ Networks; Jun. 3-5, 2006.
Steward; ZigBee Build Reliable Zigbee-Based Solutions; Apr. 16-30, 2006.
Texas Instruments; Choose your ZigBee Solution with TI; Jul. 2, 1905.
Texas Instruments; Consumer Medical Applications Guide; Jul. 2, 1905.
Texas Instruments; RF/IF and ZigBee® Solutions; Dec. 8, 2010.
Texas Instruments; ZigBee® Wireless Networking Overview; Jul. 2, 1905.
The Nokia Network Monitor; Oct. 30, 2005.
Unknown Author; TutorialReports.com; Zigbee Tutorial; Nov. 1, 2010.
Versel; ZigBee Alliance Ratifies Wireless Protocol for Low-Power Medical Devices; Apr. 6, 2010.
Wellspring; Router, Tageway, Base Station, Cell Modem Specification and Submittal; Jan. 1, 2011.
Wellspring Switches to a ZigBee-Cellular Hybrid System; Feb. 20, 2006.
Zigbee; Wireless Sensor Applications for Health, Wellness and Fitness; Mar. 1, 2009.

\* cited by examiner

NETWORKED SYMBIOTIC EDGE USER INFRASTRUCTURE

CROSS-REFERENCE TO RELATED APPLICATIONS

This application claims priority from U.S. Provisional Patent Application No. 61/159,600, filed Mar. 12, 2009, incorporated herein by reference in its entirety for all purposes.

BACKGROUND

As is known in the art, medical first responders perform a variety of tasks outside of a hospital in both military and non-military (e.g., governmental, civilian and commercial) settings. Such tasks include but are not limited to: health assessment and troop training; providing first aid to armed forces; providing first aid to civilians; providing first aid to youth and elderly; and providing humanitarian aid, as well as diplomatic and civilian support. Such tasks may be performed when a medical first responder is in a vehicle or on foot. Most of these tasks require operations where the hands of the medical first responder are actively engaged or the medical first responder's attention is critically focused on some activity. Therefore, requiring help to come from hand interactive systems diverts such responders from their necessary and very often critical duties. In general, this problem exists for all operations for which personnel are actively engaged either with their hands in general or their overall critical attention.

One goal of medical first responders is to reduce the amount of time from trauma to treatment. In combat as well as civilian medical scenarios, the first hour after trauma is sometimes referred to as "The Golden Hour" as response/treatment to trauma within this hour generally results in an improved end result for the patient. Similarly there are conditions of "platinum minutes" in the trauma domain where focused response is essential.

As is also known, there exists a class of medical systems (sometimes referred to as "mobile communications systems" or "mobile processing systems" or "edge user processing systems") which are used outside of a hospital or other medical facility (e.g., in the field and mobile). These systems often utilize terminal-based technologies and devices (e.g., laptop computers or hand-held personal digital assistants (PDAs)) which can distract medical personnel from the necessary task of patient treatment. Consequently, those types of devices may be ignored until well after an event. Thus, present edge user approaches for patient care often still rely upon paper and simple general purpose PDAs.

At present, hands-free devices that are used within a medical care context are used for one-way patient monitoring only. They collect data from the patient and transmit the collected data to a, more than often, remotely located medical care provider for off-line analysis.

SUMMARY

In one aspect, a system includes at least one first user component configured to be coupled to a first user and second user components worn by a second user and connected to a first personal area network. In the system, at least one of the second user components and the at least one first user component are configured to establish communications with each other through a first wireless network when the at least one first user component is coupled to the first user.

Embodiments may include one or more of the following features. The system may further include third user components worn by a third user who is a peer of the second user and connected to a second personal area network. The first personal area network and the second personal area network may be configured to establish communications with each other through a second wireless network. The system can also include a communications adapter configured to establish communications with each of the second and third user components through a third wireless network. The communications adaptor may be further configured to connect to a legacy infrastructure and provide for flow of information between each of the second and third user components and the legacy infrastructure. The first user may be a patient, and the second and third users may be medical first responders.

In another aspect, a system for use by a medic includes a head set assembly as well as one or more wearable intelligent associates. Each is configured for wireless communications.

In yet another aspect, a wearable computer device for use by a medic includes a memory, a processor and software stored in the memory and executable by the processor. The device further includes a wireless interface to connect wirelessly to devices worn by patients, other medics and at least one adapter that connects to a legacy infrastructure. The software includes communications protocols software and applications that, in conjunction with the wireless interface, enable the wearable computer device to exchange information with all of the devices in a manner that assists the medic as well as the other medics and personnel associated with the legacy infrastructure.

These and other features offer an edge user such as a medical first responder a hands-free operations solution that supports the edge user in an assistive manner. It provides a symbiotic, flexible, adaptive, intelligent information processing base and supporting infrastructure for edge users, and cooperative communities of edge users who need to keep their hands free for use in their particular role. In the medical community, such a solution will reduce the amount of time for treatment to begin following trauma occurrence (that is, reduce the "Golden Hour" impact) by improving the dissemination and availability of information throughout the health care process.

BRIEF DESCRIPTION OF THE DRAWINGS

The foregoing features of this invention, as well as the invention itself, may be more fully understood from the following description of the drawings in which.

DETAILED DESCRIPTION

Figure 1:
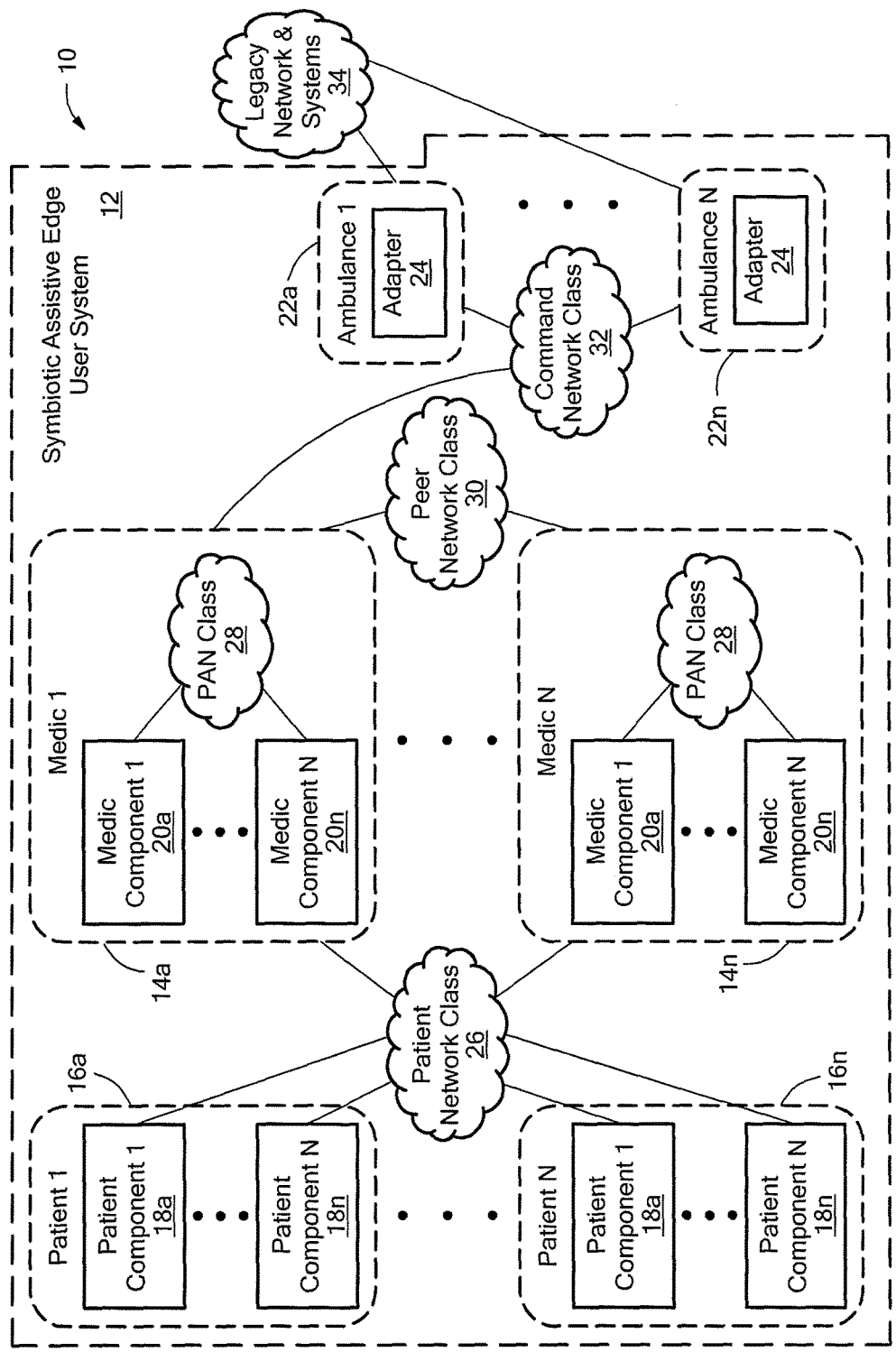
FIG. 1 illustrates a system that includes a networked symbiotic edge user system for use by medic edge users.

Referring to FIG. 1, a system 10 includes a networked symbiotic edge user system 12 (or "edge user system"). The edge user system 12 is configured to support operations of a medical first responder such as a medic (as shown) or an emergency medical technician (EMT). It should, however, be appreciated that the architecture of the edge user system 12 is not limited to use in a medical field or a medical setting, nor is it limited to use by the military. Rather, the architecture finds application in a wide variety of settings including but not limited to mechanical maintenance and repair, warehouse operations, legal environments, police, firemen, SWAT, civil engineering, regular military, office environments, commercial/general public personal use, nuclear/power environments, electrical power environments, public works environments, education/schools, and diplomatic services.

Still referring to FIG. 1, the edge user system 12 is generally configured to enable one or more medics, for example, medics 14a . . . 14n (generally denoted 14) to provide medical assistance to one or more patients 16a . . . 16n (generally denoted 16) through various networks of devices. Those devices include, for each patient 16, patient components 18a . . . 18n (generally denoted 18). The patient components 18 are attached to or otherwise associated with patients 16. Each patient 16 may be provided with one or more patient components 18. The number and type of patient components 18 may vary from patient to patient. That is, each patient 16 may have a uniquely different patient component or a uniquely different combination of patient components 18 associated with that patient. The devices also include, for each medic 14, medic components 20a . . . 20n (generally denoted 20). The medic components 20 are worn or otherwise coupled to medics 14. Each medic 14 may be provided with one or more medic components 20. Other devices can include wireless equipment located in patient evacuation/transport vehicles, such as land vehicles, e.g., ambulances 22a . . . 22n (generally denoted 22), as shown, or air vehicles, e.g., helicopters, or stationary areas. The wireless equipment, shown in the figure as an adapter 24, is capable of connecting the edge user system 12 to other, more remote networks and systems. There is an adapter 24 associated with each ambulance 22.

The interconnectivity of the system's users, i.e., the medical first responder edge users (such as medics and EMTs) and their patients, is achieved through the use of their respective devices in conjunction with various classes of networks. In the edge user system 12, as depicted in FIG. 1, each network "cloud" represents a "network class". The term "network class", as it is used herein, refers to a base environment for potential device interactions according to purpose or need. The network classes or base environments supported by the infrastructure of the edge user system 12 include: a patient network class 26 for interactions between devices of first responder and subordinate entities, e.g., medic-to-patient/patient-to-medic; a personal area network (PAN) class 28 for interactions among the medic components worn by a particular medic; a peer network class 30 for interactions between devices of peer entities, e.g., medic-to-medic; and a command network class 32 for interactions between devices of medics and superior entities, e.g., medic-to-ambulance/ambulance-to-medic.

A network medium is the base transfer mechanism through a network class, that is, the protocol used within the network class. The network medium for each of the patient network, PAN, peer network and command network environments is based on a wireless network protocols technology such as Bluetooth, ZigBee (IEEE 802.15.4), Ultra-WideBand or WiFi (IEEE 802.11), among others, or may be a combination of one or more such technologies. A network is the specific interconnection of the devices through the network medium. The devices, at the time they are connected, are part of a specific network. Those devices can be said to be connected to that network. Thus, patient components 18 and medic components 20 may connect to form a "patient network". Similarly, medic components 20 and adapters 24 can connect to form a "command network". Medic components 20 of at least two medics 14 can connect to form a "peer network". The medic components 20 worn by a particular medic are connected in a PAN. Unlike the other networks, which are of an ad-hoc nature, each medic's PAN is relatively static in its topology. Patient networks, PANs and peer networks may make use of a short-range, proximity-based wireless protocol like Bluetooth. A command network may utilize a protocol more suitable for longer distances and higher bandwidths (e.g., WiFi). It will be understood that each device associated with a particular network class (and corresponding type of network, once formed) will be configured with the appropriate wireless interface and software to implement the wireless communications protocols used within that network class.

In one embodiment, and as illustrated in FIG. 1, the system 10 includes legacy networks and systems 34 (or "legacy infrastructure" 34) with which the edge user system 12 must interact. The adapter 24 serves as an interface between the edge user system 12 and the legacy infrastructure 34, and therefore has the capability to convert the communication protocols of one to those of the other. Thus, the adapter 24 may take the form of a router or other network device that can perform this function.

The architecture of the edge user system 12 allows information collected by/provided to the medic components 20 to be transmitted "upstream" to the legacy infrastructure 34. The legacy infrastructure 34 can include networks and systems of medical facilities (e.g., aid stations, hospitals, etc.), and in a military context, command operations facilities as well. The edge user system 12 also allows for a flow of information in the opposite, or "downstream", direction as well. As will be discussed in more detail later, the adapter 24 can be implemented to act as an information "advocate" on behalf of downstream devices such as the medic components 20. As an advocate, the adapter 24 can help move information downstream from the legacy infrastructure 34 to medic components 20 in a manner that anticipates the information needs of those components.

As discussed above, the patient components 18 and the medic components 20 can be configured to utilize a short distance wireless connection to communicate with each other. The patient components 18 provide patient information over that connection to at least one of the medic components 20. Once the information is provided to a medic component 20, the medic 14 to whom the medic component 20 is coupled can access the information.

The architecture has application in both military and civilian medical settings even though the operation models differ. For example, in a military operations model, the field medic stays with his/her squad. The patient is first treated by the medic and then transferred to evacuation personnel ("evacuation vehicle" like ambulance 22). The patient is transported to an aid station, where aid station personnel take over the care of the patient. After the aid station, the patient may be transferred to a hospital for additional medical care. In contrast, in a civilian operations model, the EMT travels in the ambulance to the patient's location, treats the patient on-location and then accompanies (as well as continues to treat/monitor) the patient in the ambulance to the hospital emergency room (ER). Also, it will be appreciated that the architecture could be easily extended from operations of medic/EMT in "the field" to those of aid station personnel and evacuation personnel in the military operations model, as well as EMT providing care in an ambulance in the civilian operations model.

Figure 2:
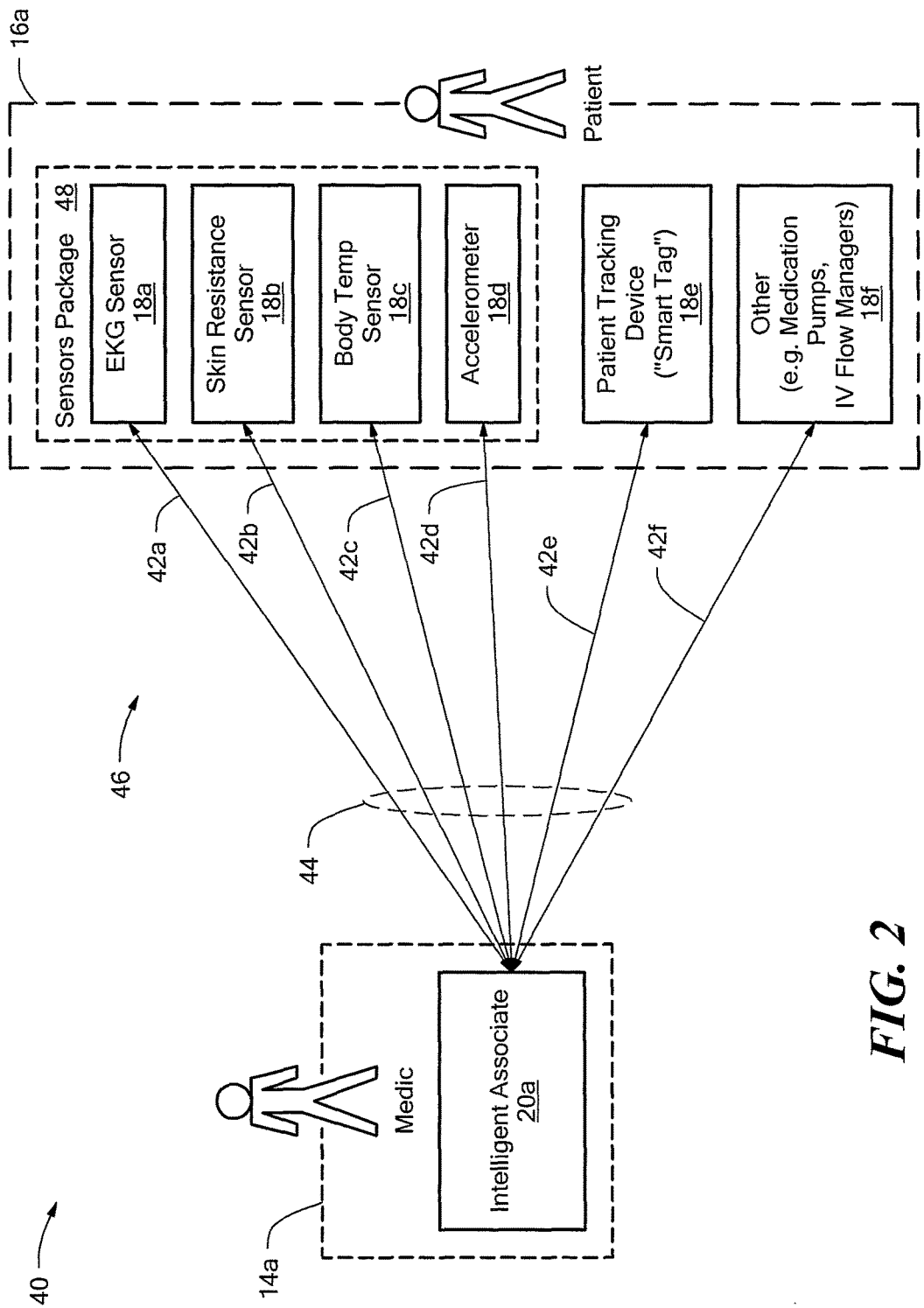
FIG. 2 illustrates an exemplary patient network usable for patient-medic communications in the networked symbiotic edge user system.

FIG. 2 shows an example of a wireless patient network 40 formed when a medic component, shown here as an intelligent associate 20a associated with a medic (e.g., medic 14a), is communicating with a number of patient components 18a, 18b, 18c, 18d, 18e, 18f of a patient 16a via respective communication connections (or links) 42a, 42b, 42c, 42d, 42e, 42f (collectively, connections 44). The connections 44 support transmission of information through a transmission medium 46 according to desired communications protocols. In this example, the patient components 18a-18f include various patient sensors, such as an ECG sensor corresponding to patient component 18a, a skin resistance sensor corresponding to patient component 18b, a body temperature sensor corresponding to patient component 18c and a movement/activity sensor (accelerometer) corresponding to patient component 18d. Sensors to monitor other physiological parameters, such as heart rate, respiration rate, hydration level, pulse, oxygen level and others, may be included. These patient sensors may be coupled to the patient individually or packaged together in a single unit, e.g., telemetry system or sensor package 48, that allows immediate and continuous monitoring of patient vitals. An individual sensor or sensor package 48, if designed as a single wireless adherent device, may be referred to as a "sensor patch". Other patient components may include a patient tracking device or "smart tag" 18e (corresponding to patient component 18e), which is a continuous patient level record and information management device that stays with patient, as well as other patient monitoring devices or accessories (corresponding to at least one other patient component 18f), e.g., medication pump, IV flow manager, blood pressure cuffs, oxygen flow meters, intelligent stretcher, real-time monitoring undergarment (for continuous health monitoring of the patient) and the like. A device representative of the type of "sensor patch" that might be used in this architecture is provided by Coventis, Inc. Other wireless sensors, tracking devices and patient accessories may, of course, also be used.

The particular set of patient components applied to one patient may differ from those applied to another patient. Thus, and referring back to FIG. 1 in conjunction with FIG. 2, one patient, e.g., patient 16a, may be provided with a sensor patch while a second patient, e.g., patient 16b, may be provided with a smart tag (or, alternatively, a smart tag and a sensor patch). It is possible to envision a more likely scenario in which each patient is provided with a smart tag to associate a record/identification with that patient, at minimum, and further provided a sensor patch to monitor overall vital signs. Other devices could be applied to a patient based on that patient's unique medical condition. For example, a third patient 16n with brain trauma could be provided with a "smart skull cap" to monitor brain activity as well.

Thus, the edge user system 12 incorporates the functions provided by various patient components 18 to address traumatic event response. Although not illustrated in FIG. 2, there may be some level of interconnectivity supported between various patient components 18 as well, if they are configured for such operation. For example, the patient components 18 may be configured to support connections between the smart tag 18e and each of the other patient components, as described later with reference to FIG. 12.

Figure 3:
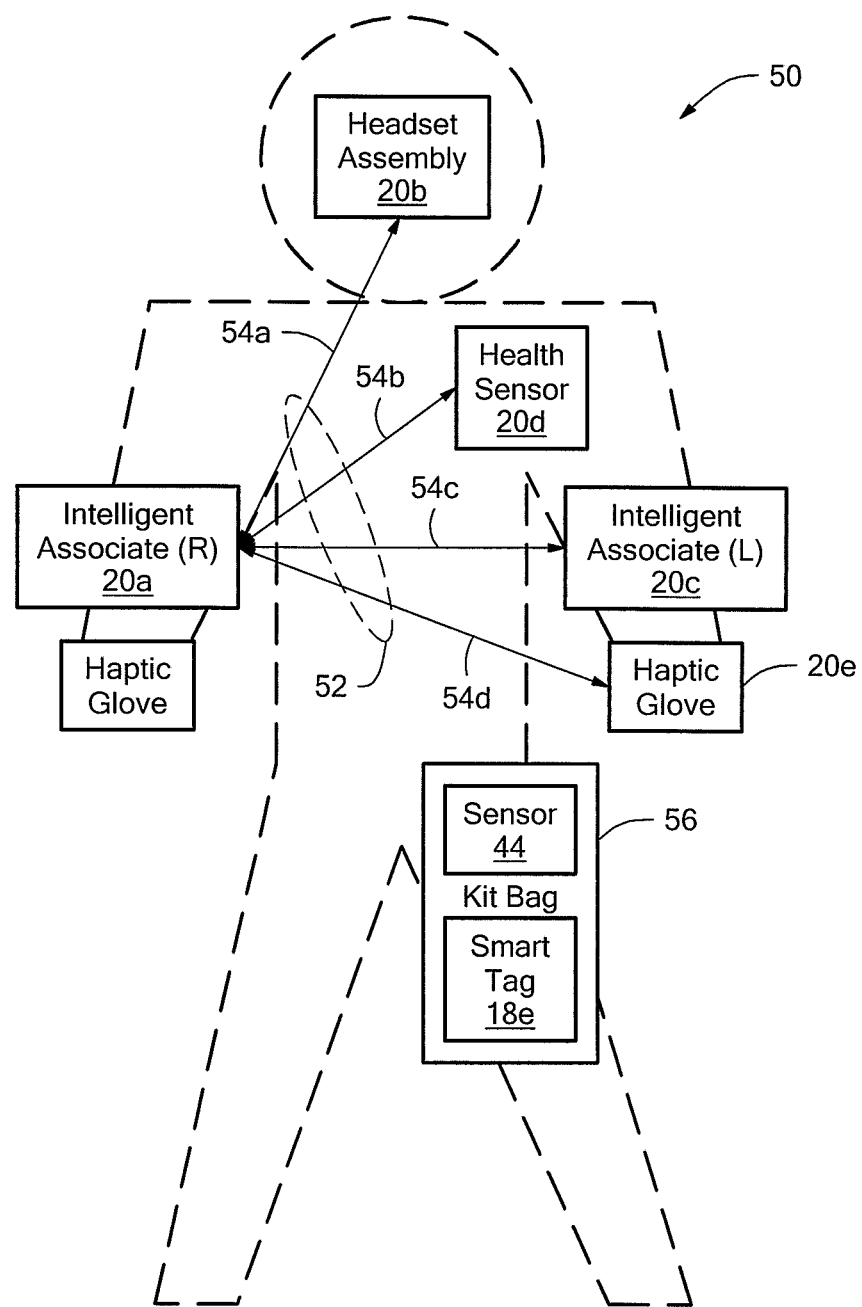
FIG. 3 illustrates an exemplary personal area network (PAN) associated with a medic.

FIG. 3 shows an exemplary wireless medic-associated personal area network (PAN) 50. In the illustrated example topology, the PAN 50 includes as its "nodes" the following medic components 20: an intelligent associate 20a, a headset assembly 20b and a second intelligent associated 20c. Other nodes can include, for example (and as shown), at least one medic health sensor 20d to monitor the health of the medic, and one or more haptic gloves 20e. The PAN 50 can be further and naturally expanded with other options, such as one or more environmental sensors (e.g., meteorological, chemical, biological and radiological sensors) or effectors (e.g., RF jammers).

The medic components of PAN 50 begin communications as soon as they are within range (practically speaking, when the medic puts on the necessary gear). In the illustrated embodiment, one of the intelligent associates, e.g., intelligent associate 20a, communicates with each of the other medic components in the PAN 50. Thus, in the illustrated PAN 50, there would be connections 52 formed between the intelligent associate 20a and the other medic components of the PAN 50. That is, the intelligent associate 20a would be connected to the headset assembly 20b, the health sensor 20d, the other intelligent associate 20c (if more than one intelligent associate is used) and the haptic glove(s) 20e via respective connections 54a, 54b, 54c, 54d. In addition, a medic can carry in a kit bag 56 various sensors and smart tags of the type shown in FIG. 2, e.g., sensor patch 48 and smart tag 18c, to apply to patients at the time the medic encounters and begins treating them. Other PAN medic components 20 can include, for example, personal digital assistant (PDA), laptop, cell phone, undergarment for monitoring vital signs and other peripheral, storage or computing devices.

Although not shown, intelligent associate 20c, like intelligent associate 20a, may be connected directly to each of the medic components of the PAN. Alternatively, only intelligent associate 20c may be connected to each of the other devices. While intelligent associates 20a, 20c may be identical in physical form and capability, they may be configured to have different roles within the PAN or in their interactions with other networks within the edge user system 12. For example, in one configuration, one intelligent associate may be configured to connect to patient components 18 as part of a patient network and to connect to a medic component 20 worn by another medic 14 as part of a peer network. In that same configuration, the other intelligent associate may be configured to connect to the other medic components 20 of the PAN in which it resides, as well as connect to a "superior" entity device via a higher level network class such as command network class 32, e.g., adapter 24 (shown in FIG. 1), and thus participate as a node in a command network. The intelligent associate configurations can be implemented to support workload sharing (e.g., one could be responsible for main display and communications activities while the other handled support display and processing/memory activities), shadowing, redundancy or other desired functions between the two intelligent associates of a given PAN (or with the intelligent associates of a peer medic). While two (arm-worn) intelligent associates are shown, additional intelligent associates designed to be worn or coupled to other parts of medic's body could be used as well. The devices' capabilities could be shared among all of the intelligent associates, including those that are arm-worn and those that are not arm-worn.

The location of certain capabilities can be determined by user interactions or other factors for a given application. For example, in an application where only one intelligent associate is used and is expected to be worn on the left arm to free up the right arm for other purposes, the left arm component may be patient-oriented. Communications may be distributed to minimize energy consumption (as some types of communications, e.g., command network related communications, may use more power than other types of communications, e.g., patient and peer related communications). Alternatively, a single communications structure in each intelligent associate could support multiple channels using independent protocols, ranges, data rates, etc., upon demand. With such a structure, any intelligent associate could be adapted to the network interfaces that are needed (patient, peer, command, PAN), thereby increasing overall flexibility and reliability.

The PAN architecture can be adapted to include any other personal telemetry or effector systems using the same communications media. The flexible nature of the architecture allows the wearer to alter capabilities and roles as the situation requires. For example, the medic could wear an audio interface "clip" that would have a speaker and microphone for interacting with locals using different languages, or could attach specific chemical, biological, or radiological sensors when entering a potentially hazardous environment.

In some wireless embodiments, and referring to FIG. 1 in conjunction with FIGS. 2-3, components worn by patients 16 and medics 14 automatically sense each other according to proximity-based communications protocols supported by the architecture of the edge user system 12. That is, the sensing will occur as a medic approaches a patient, assuming the patient already wears at least one patient component. If the patient component(s) 18 of a patient and at least one medic component 14 of a medic need to interact, they begin exchanging information via the patient network environment 26. Each recognizes the other and applies policies to determine if they need to interact. Using communications capabilities of an existing wireless protocol standard such as Bluetooth requires reliance on that standard's features at the lowest level of implementation. Thus, in one embodiment, the patient components 18 are "queried." The architecture of the edge user system 12 can allow communications via other, more efficient, protocols, however. It should be appreciated that the level of involvement which may be needed from a user (e.g., a medic 14) to support the automatic recognition of patient components 18 and configuration of a patient network such as patient network 40 (from FIG. 2) with those patient components is directly related to the limitations of the protocols for the implemented communications standard, although the architecture allows for complete autonomy in this recognition process.

Figure 4A:
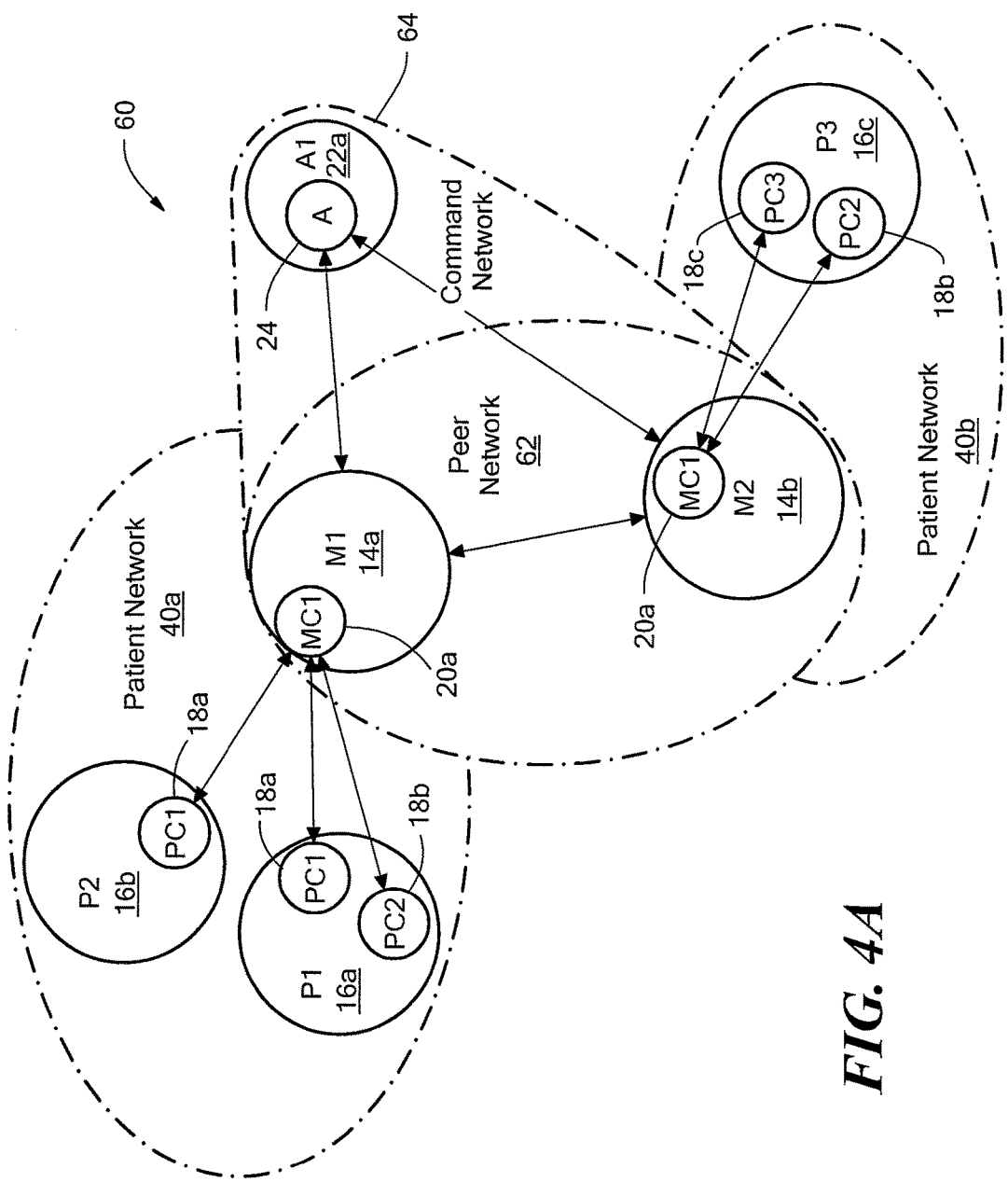
FIGS. 4A-4C illustrate example ad hoc network configurations that can occur within the networked symbiotic edge user system.
Figure 4B:
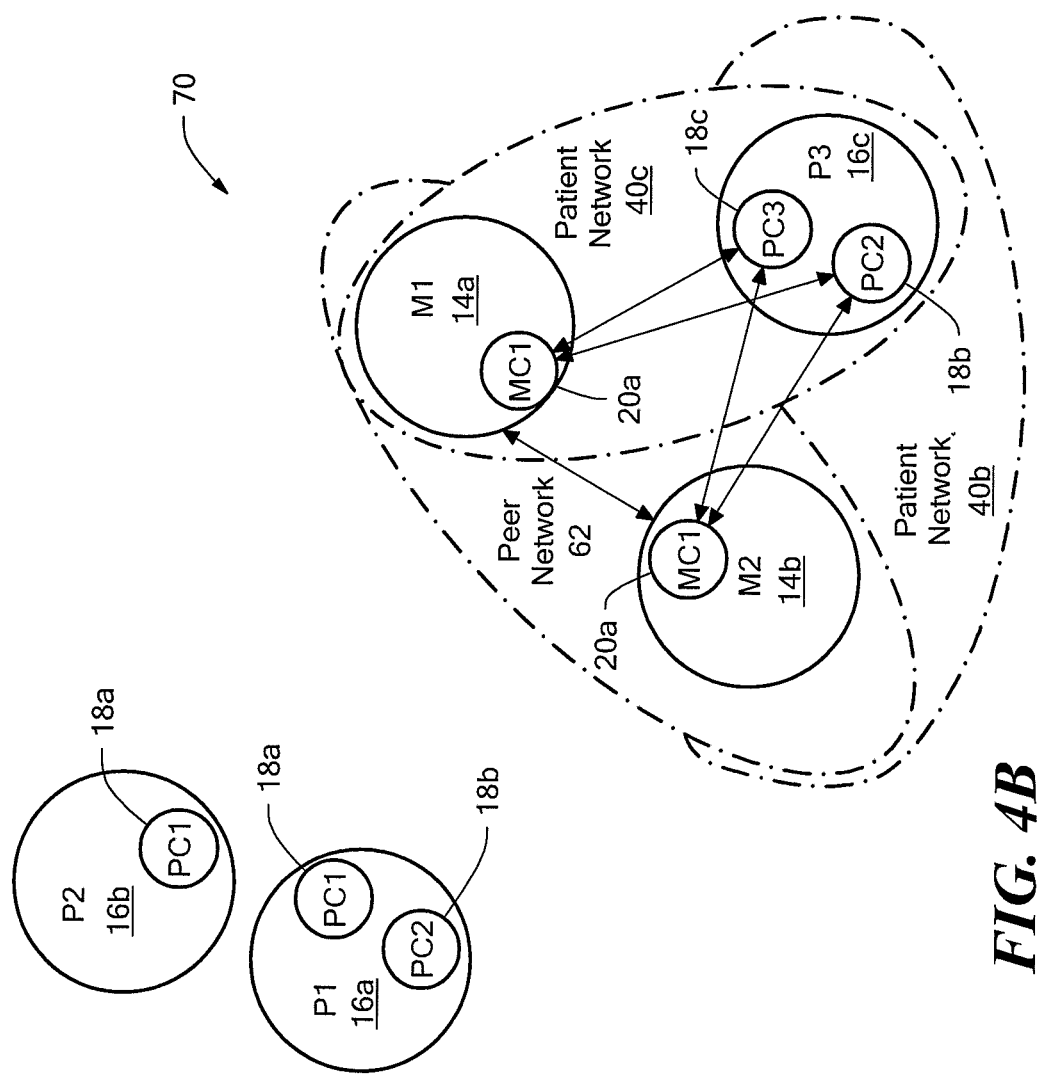
Figure 4C:
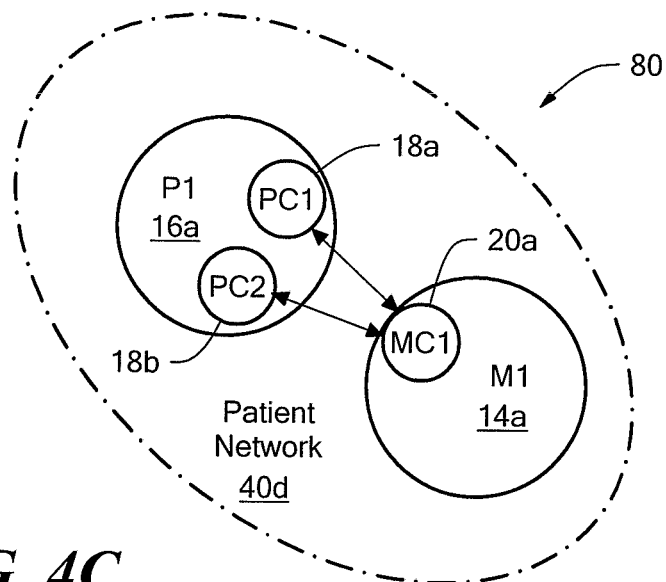

The formation of the various classes of networks, in particular, patient networks, tends to be dynamic in nature, as illustrated in FIGS. 4A-4C. Referring first to FIG. 4A, a first configuration 60 involves a first medic "M1" 14a, second medic "M2" 14b and three patients shown as a first patient "P1" 16a, a second patient "P2" 16b and a third patient "P3" 16c. Associated with the first medic 14a is at least one medic component shown as first medic component "MC1" 20a. There is also at least one medic component, again shown as first medic component "MC1" 20a, associated with the second medic 14b. Associated with the first patient "P1" 16a are two patient components 18a, 18b. Associated with the second patient "P2" 16b is just one patient component "PC1" 18a. Like the first patient 16a, the third patient 16c has been provided with two patient components, shown as patient components "PC2" 18b and "PC3" 18c.

Based on at least the proximity that exists between the first medic 14a and patients 16a, 16b when the first medic 14a approaches those patients, first medic component "MC1" 20a and the three patient components of patients 16a, 16b can connect with each other to form a first patient network shown as patient network 40a. In the illustrated example, connections are established between medic component "MC1" 20a and each of the three patient components, that is, patient components 18a, 18b of patient 16a and patient component 18a of patient 16b. The patient components on patients 16a, 16b begin transmitting patient information to the medic component 20a worn by medic 14a. Such information could include, for example, heart rate, respiration rate, patient activity, body core temperature, hydration levels and ECG and other data, based on the type(s) of patient components 18 being used. The medic component 20a worn by medic 14a could send acknowledgements and mode command changes to all the patient components. For smart tags, the communications from a medic component could also include, e.g., patient record updates and specific treatment control algorithms/parameters as appropriate.

Similarly, as the second medic 16b approaches the third patient 16c, their respective components can connect to form a second patient network shown as patient network 40b. Connections are established between medic component 20a and each of the patient components 18b, 18c of patient 16c.

Assuming the medics 14a and 14b are in close enough proximity so that their respective medic components are within the required range to establish communications with each other, a third network shown as peer network 62 may be formed. In the peer network 62, a connection is established between medic components of the two medics. Depending on the wireless technology or technologies used, that connection may be between the medic component 20a for medic 14a and the medic component 20a for medic 14b, or between an alternate pair of medic components not shown.

Also shown in FIG. 4A is an exemplary command network 64 that is formed by interconnected nodes including medic components of the two medics 14a, 14b and a third node "A" corresponding to the adapter 24 of an ambulance "A1" shown as ambulance 22a. Connectivity between adapter and medic (more specifically, medic components) is not necessarily controlled by range. The communication links between devices participating in the command network 64 may be established according to protocols defined to accommodate greater distances between nodes, such as wireless LAN or WiFi protocols.

FIGS. 4B and 4C illustrate how the configuration or topology of an edge user system changes as medics and, in some cases, patients, change locations and interactions. The command network 64 from FIG. 4A has been omitted from FIGS. 4B and 4C for purposes of simplification. If included, it would be as shown in FIG. 4A.

Referring now to FIG. 4B, in a second configuration 70, when medic 14a moves away from patients 16a, 16b toward another patient, e.g., patient 16c (as shown), the medic component 20a on medic 14a automatically drops its connections with the patient components 18a, 18b on patient 16a and patient component 18a on patient 16b (assuming the patient components of patients 16a and 16b are now outside of range of the medic 14a), and may add connections to the patient components 18b, 18c on patient 16c (which is now within range of the medic 14a). Again, connectivity is mainly controlled by range. As long as communications are within range, the patient components 18b, 18c on patient 16c are able to interact with the medic component 20a on medic 14a as part of a new, third patient network 40c while at the same time maintaining communications with the medic component 20a on medic 14b as part of the second patient network 40b.

Referring to FIG. 4C, in a third configuration 80, the medic 14a moves back in range of patient 16a. Thus, the patient components 18a, 18b on patient 16a are recognized by the medic component on medic 14a, which is then reconnected with them. In this particular configuration, it is assumed that patients 16b and 16c have been transported to other locations and medic 14b is no longer operating in the vicinity of medic 14a. If both patients 18a, 18b had been stationary, the original patient network shown in FIG. 4A would have been re-established.

Unlike the medic's PAN, which remains more or less static in topology for the time(s) that the medic is treating patients in the field (unless the medic decides to remove or add a device during those times), the topology of the patient network changes over time. That is, the patient network is "grown" at the time of application of the individual patient components to patients by a medic.

It can be seen from the illustrative configurations 60 70, 80 of FIGS. 4A-4C that one or more ad-hoc networks can be formed as medics move among different patients. Networks of patient components and medic components are dynamic, not static. Also, since all patients within range will be able to be connected with a medic, and medics within range of each other can be connected together as well, a "hive" kind of connectivity sharing information from multiple patients across the various networks is achieved. When a medic moves out of range of a patient (assuming the patient is stationary), the link is lost, but the patient components still continue operations. When the medic moves back into range of that patient, the connection is re-established and the medic's records (stored locally in a medic component of that medic, e.g., the medic component that communicates with the patient components of the patient) is updated with all delta information gathered during the disconnection. In this way, as a medic moves from patient to patient, patient information is automatically transferred from the patient components to medic components.

Also, it should be appreciated that since the patient information is automatically collected, the medic need not engage in certain data collection activities and thus the medic has more time available to attend to specific patient needs and concerns. As will become apparent from the description hereinbelow, once patient information is provided to a medic component, that medic component may further process and transmit the information to additional nodes and/or networks.

The segregation of communications allows collection of information independently of connectivity. In this way, patient information collected by patient components and provided to a particular medic component (e.g., one of the arm-wearable intelligent associates shown in FIG. 3), it can be shared among multiple medic components (e.g., can be shared among multiple intelligent associates, via a medic's PAN) as well as shared among multiple medics via peer networked connections.

The architecture described herein allows the medic to provide treatment to a patient while at the same time medic worn devices collect patient information and provide the information to other medical facilities. At the same time, the medic can receive information from other sources (e.g., other medical facilities) which can aid the medic in treating patients and the medic can share such information with other medics via the peer network.

Also, as was described above, medics can move between multiple patients and collect information from patient components (such as sensors, smart tags, and the like) coupled to the patients. In this way, information concerning a particular patient can be collected and provided to medical facilities by multiple medics at the same time or at different points in time.

Figure 5:
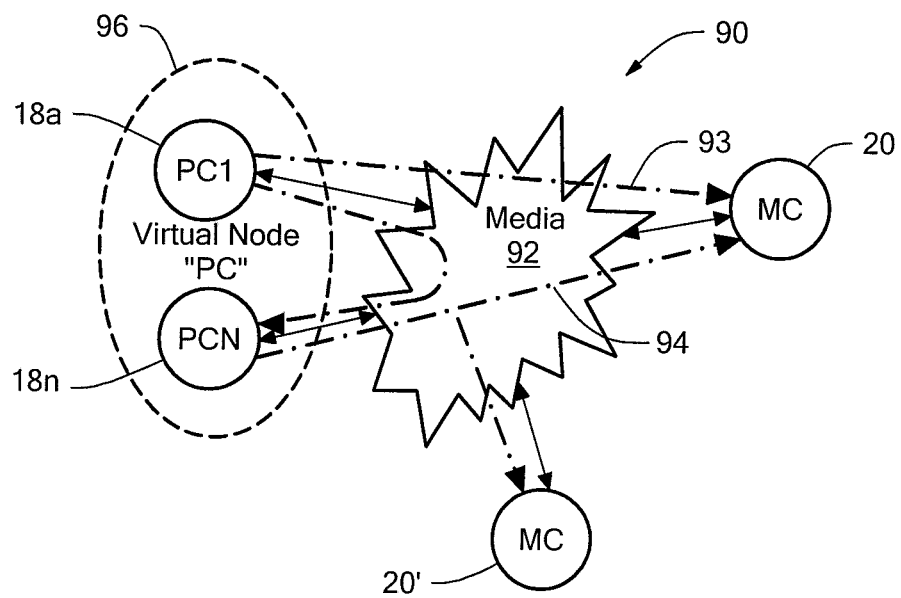
FIG. 5 illustrates sovereign systems behavior of a networked symbiotic edge user system such as that depicted in FIG. 1, according to one exemplary embodiment.

In one exemplary embodiment, and referring now to FIG. 5, the architecture of the edge user system 12 (of FIG. 1) can be implemented to support an operational pattern of nodal sovereignty. FIG. 5 illustrates how this operational pattern of nodal sovereignty applies to communications between medics and patients. Thus, in a medical instantiation of a sovereign system of nodes associated with patients and medics, a sovereign system 90 includes four sovereign nodes, with two nodes corresponding to patient components (patient component "PC1" and "PCN"), indicated by reference numerals 18a and 18n, and two nodes corresponding to medic nodes ("MC"), i.e., medic components of different medics, indicated here by reference numerals 20 and 20'. The nodes communicate with each other via media 92. An operational pattern of nodal sovereignty preserves nodal integrity by establishing communications channels in the media 92 through the mutual negotiated exchange between nodes as independent unique structures. An established channel may be a single channel, e.g., single channel 93 (between node 18a and node 20), or a shared channel, e.g., shared channel 94 (which is shared by nodes 18n, 20 and 20'). Due to the cooperative nature of the sovereign nodes, the negotiation is a mutual negotiation at the highest abstraction. Consequently, external information and media interactions are independent of, and buffered from, internal information architectures or formats. Negotiation of interfaces is outwardly controlled from each domain or territory of the node in question and doesn't have any externally managed pre-defined definitions without mutual negotiation of the participating nodes.

Virtual sovereignty is the nesting of node sovereignties. The nesting of node sovereignties allows mutual identification of abstract entities and can have various levels of negotiated alliances, relationships, and responsibilities both at the abstract level and for each participating node. Within a medical instantiation, as illustrated in FIG. 5, the various patient components 18a, 18n attached to a patient become a virtual node 96 uniquely identified with that patient. The sovereignty of information for the patient is retained within that virtual node and the unique set of physical nodes (i.e., the nodes 18a, 18n, in the illustrated topology) that are part of the patient's composition. Medic components of medics interacting with that patient, such as medic components (nodes) 20, 20' do not have to recognize the physical patient nodes 18a, 18n as separate. Rather, they recognize the physical patient nodes 18a, 18n as part of the virtual node 96.

Sovereignty therefore allows individual nodes to adopt patterns of interaction according to their own purposes but have to, by the nature of sovereignty, gain concurrence from the other sovereign nodes, to enact the pattern between cooperating nodes. This is true also when groups of nodes choose to include a new node or respond to the loss of a node's active participation. In a sovereign system, nodes can request and negotiate information rather than just accepting information pushed to them. Additionally, a sovereign system (like that depicted in FIG. 5) can recognize nodes that have been previously interacted with, thereby reducing reconnection activities (e.g., the types of mutual negotiations discussed earlier) between nodes.

Adapters 24, whose purpose is to interface with the legacy infrastructure 34, intercede to maintain sovereign actions within the sovereign system while acting as a component within the legacy infrastructure. Within the sovereign system, the adapter acts as another node, one that is an advocate of the cumulative sovereign systems capabilities to the external system and adopts the legacy systems business model at that interface point.

The sovereign system concept is applicable to any set of nodes connected across a specific wireless network. That is, it applies not only to the patient/medic relationship (as illustrated in FIG. 5) but to the peer, command, and even the personal area networks. Certain aspects illustrated in FIG. 5 such as the 'virtual node' may apply more fully to the patient network since the 'virtual node' developed by adding patient components to the patient network's node capabilities is more dynamic in its evolvement whereas the medic PAN and command network nodes tend to be less dynamic in their capability evolutions (i.e., they are "pre-set" during initial installation).

With the sovereignty approach, communications paths for the patient have the opportunity to change over time as well. Initially, patient components such as sensors and controls that are coupled with the patient communicate directly with the medic. After an appropriately capable advocacy patient component is coupled to the patient, that component can be authorized by the other patient components (on the same patient) to become the nexus for all communications with the medic. This capability provides the patient with a total network 'virtual node' that has evolved from the initial piece parts.

Although the 'virtual node' aspect of the sovereign system is most applicable to the patient side because the patient side has the most rapid operations time changes in the care of the patient, it could be applied to other nodes within the edge user system as well. Some implementations for the medic and adapter nodes may use specific, pre-defined "gateways" for interaction between the medias (patient, peer, PAN, command) to minimize power drain and costs and maximizing response of the system. However, with appropriate technology support, these other nodes and media can be provided with more flexible configurations (or migrate from pre-defined configurations to more flexible configurations) as well, with roles and dynamically derived network trees within the broader context of a wireless network environment. As a consequence, medic component nodes of each medic's PAN could appear as a virtual node to the adapter, and the medic PANs collectively could appear as a virtual node to the adapter. Similarly, multiple adapters could appear as virtual nodes to each medic's PAN.

Figure 6:
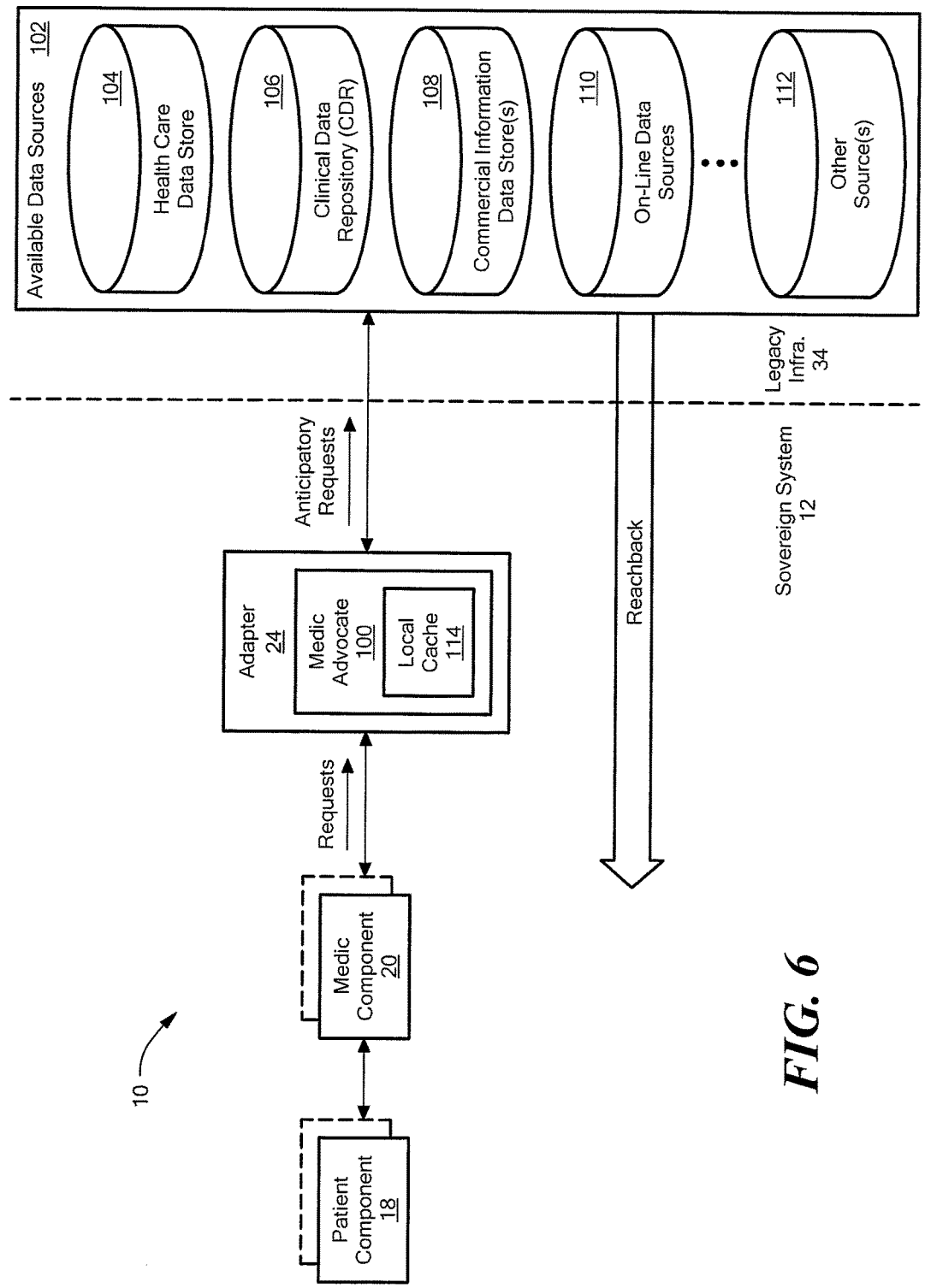
FIG. 6 illustrates an exemplary data mining capability of the networked symbiotic edge user system.

FIG. 6 shows a simplified view of system 10 that illustrates details of its data mining capability. A medic advocate 100, which may be implemented in software or combination of software and hardware, resides in the adapter 24. The medic advocate 100 is able to perform a "reachback" to bring data from available data sources 102, i.e., various databases and other data storage facilities within the legacy infrastructure 34, to medic component(s) 20. These facilities can include, for example, a health care data store 104, a clinical data repository (CDR) 106, one or more commercial information data stores 108, on-line data source(s) 110, and other sources 112. The health care data store 104 may be a data store that stores individual patient encounter records. The CDR 106 may be a data repository that stores life-long medical patient records. The commercial information data stores 108 can include any type of commercially available database containing information that would be useful to a medical first responder. One example might be a database that contains information on drugs, poisons and illnesses (e.g., MICROMEDIX, developed by Thompson MICROMEDIX). Other types of data sources could, for example, store information concerning medical situational awareness, medical reference tools (to provide information about worldwide diseases, environmental risks and countermeasures), and cultural and geographic information. The reachback of the data mining can utilize various tools and utilities, such as artificial intelligence (AI) and caching, to allow the advocate 100 to retrieve information from upstream data sources 102 that anticipates the needs of downstream entities such as the medic components 20, in particular, intelligent associates of medics.

Data mining within the sovereign system is a distributed function defined and executed by node roles. An adapter to the sovereign system anticipates information and knowledge needs via shared information or requests between the legacy and sovereign system's domains and therefore mines and caches information local to itself, e.g., in local cache 114, in response to that anticipation. This information mining is also exhibited locally to any physical node as part of its role and purpose. By distributing this capability in a mutually supportive manner, time for information access is improved while maintaining the individual nodes local ownership and management of its decisions and needs.

Thus, the adapter 24 provides an adaptive interface (between the edge user system 12 and legacy infrastructure 34), to intercede for the networked symbiotic edge user system 12 and intelligently negotiate the interactions with and mine the knowledge held by the legacy infrastructure. This functionality eliminates the need for the medic or patient subsystems to adapt to or even be aware of the specific natures of existing infrastructures.

Exemplary details and features of various medic components and patient components that can be used in an edge user system like edge user system 12 will now be presented with reference to FIGS. 7-12.

Figure 7:
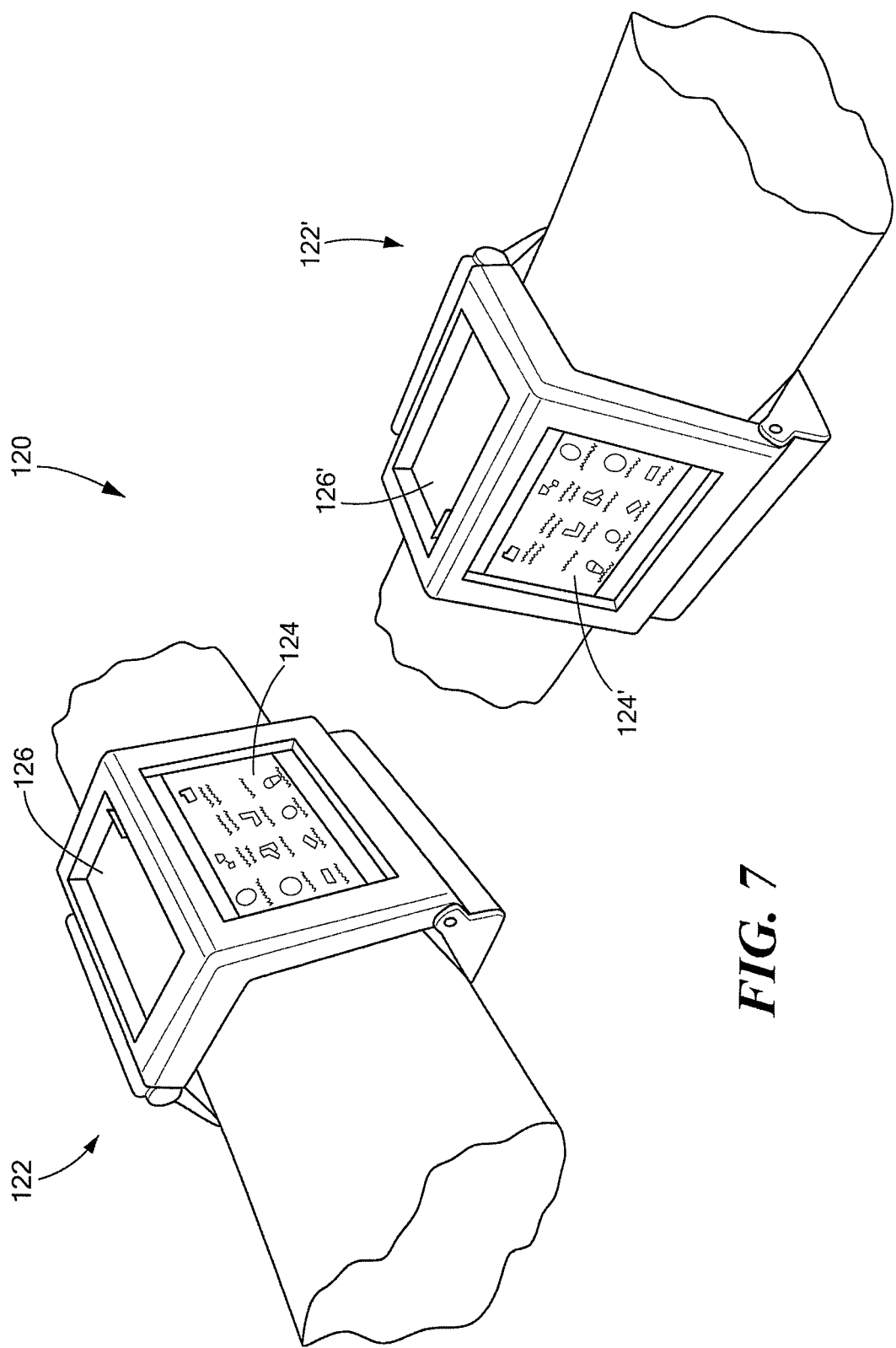
FIG. 7 illustrates a pair of arm-wearable intelligent associates for use in a PAN like that shown in FIG. 3.

Referring to FIG. 7, a pair of intelligent associates 120 includes a first intelligent associate 122 to be worn on a medic's left arm and a second intelligent associate 122' designed to be worn on the medic's right arm. Intelligent associates 122 and 122' (generally denoted 122) correspond to intelligent associates previously shown as intelligent associates 20c and 20a, respectively, from FIG. 3. In one embodiment, as shown, the intelligent associates are provided as so-called vambraces 122. In the illustrated embodiment, the vambrace can include one or more displays, for example, a main display (main displays 124, 124' for vambraces 122, 122', respectively) and a secondary display (secondary displays 126, 126' for vambraces 122, 122', respectively. The vambraces 122 are intelligent, wearable computers. In the edge user system context, the term "intelligent" refers to certain capabilities of the device. For example, its operations can include the application of algorithms in information management and decisioning theory to interpret data based on context, constraints and other conditions. Also, it can perform operations of an associative or assistive nature, e.g., continuously monitoring the activities of the wearer, and the flow and content of information it sees from communications and other telemetry to anticipate role needs and stage next step support (i.e., assistive by monitoring of the available information through the application of several potential algorithmic reasoning and pattern recognition constructs such as "fuzzy logic", inference models, etc.).

Figure 8:
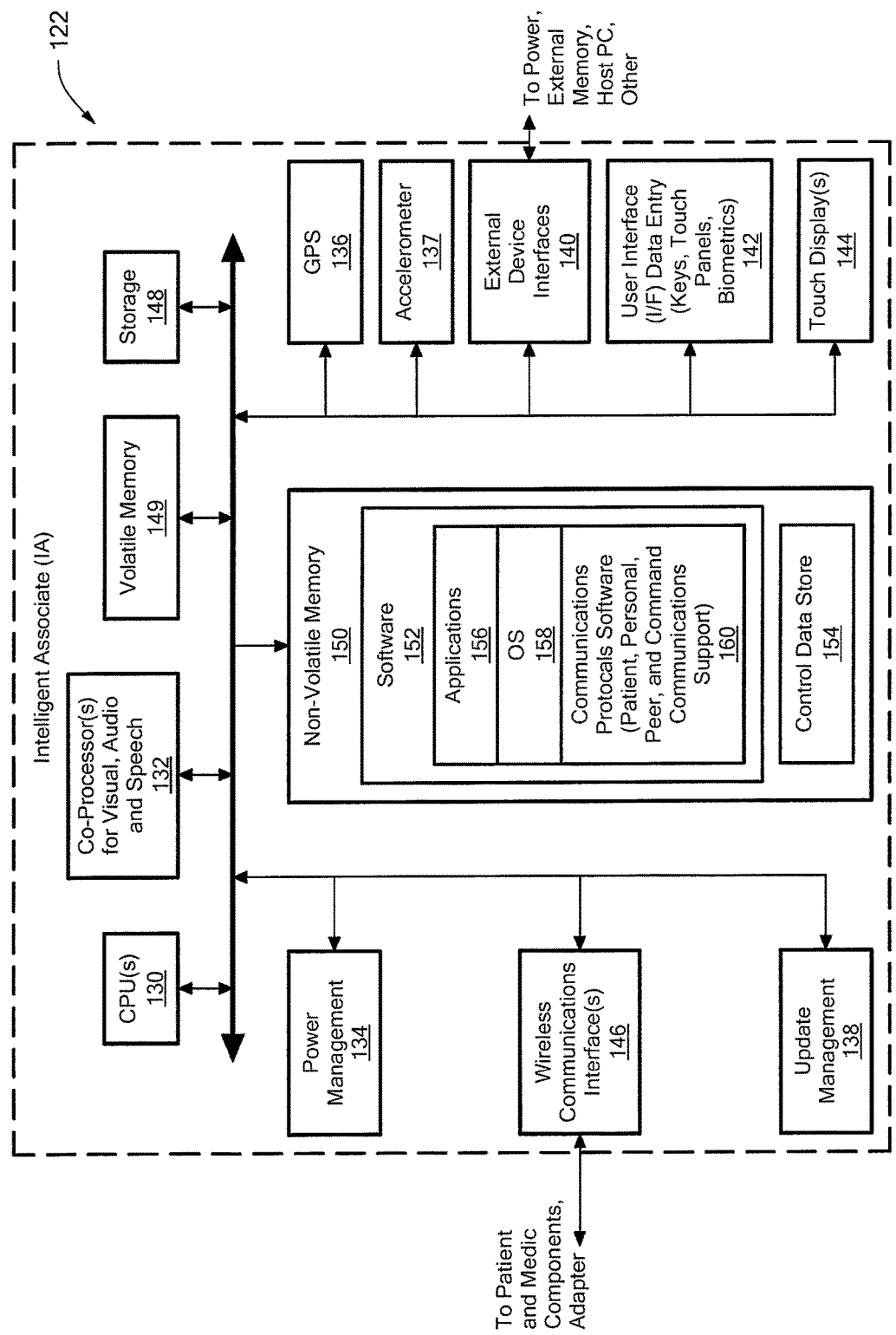
FIG. 8 illustrates an exemplary architecture of the arm-wearable intelligent associates shown in FIGS. 3 and 7.

FIG. 8 shows a simplified functional block diagram of the intelligent associate (IA) 122. The IA 122 includes various processing devices, including, for example, one or more CPUs 130 and co-processors 132 dedicated to performing visual, audio and speech related processing. The IA 122 includes power management logic 134, GPS 136 (for location detection), an accelerometer 137 (for orientation and motion detection) and update management 138. Also included are various interfaces, including external device interfaces 140 to allow connections to external power devices, memory, host PCs, and other devices, as well as user interfaces 142 (e.g., data entry interface such as keys, touch panels, biometric fingerprint sensor, etc.) and touch displays 144. Other interfaces include communications interfaces 146 (to provide the wireless protocols transport and lower level communications support for connecting to patient and medic components, as well as adapter 24 (from FIG. 1). The IA 122 provides hard disk storage 148, volatile memory 149, as well as nonvolatile memory 150 to store software 152 and control data store 154. The software 152 includes applications 156, operating system 158 (e.g., Linux Kernel) as well as communications protocols software 160 to support the type of personal, patient and command network communications interactions, including sovereign system behavior, discussed earlier. The software 152 would be copied to the volatile memory 149 (or internal CPU memory) for subsequent execution by the CPU 130. The various functional blocks of the IA 122 are coupled to an internal bus structure, shown here in simplified form as interconnect 162. The internal bus architecture could be implemented any number of ways according to design requirements and known bus design techniques.

The communications protocols implemented by the communications protocols software 160 may be distributed across one or more protocol layers of whatever protocol stack (e.g., the Open Systems Interconnection or "OSI" reference model) that is used. In one embodiment, the distribution may be limited to lower protocol layers implementing existing lower level protocols (such as Bluetooth, WiFi, etc.). In other embodiments, the communications protocols may be further distributed at other layers to support more advanced communications capabilities such as the sovereign system behavior described earlier. The protocol stack itself may reside in the OS, or it may be implemented in separate modules and drivers. It will be understood that each component, e.g., patient component 18, medic component 20 and adapter 24, with which the IA 122 communicates would include the same or similar communications protocols software.

Figure 9:
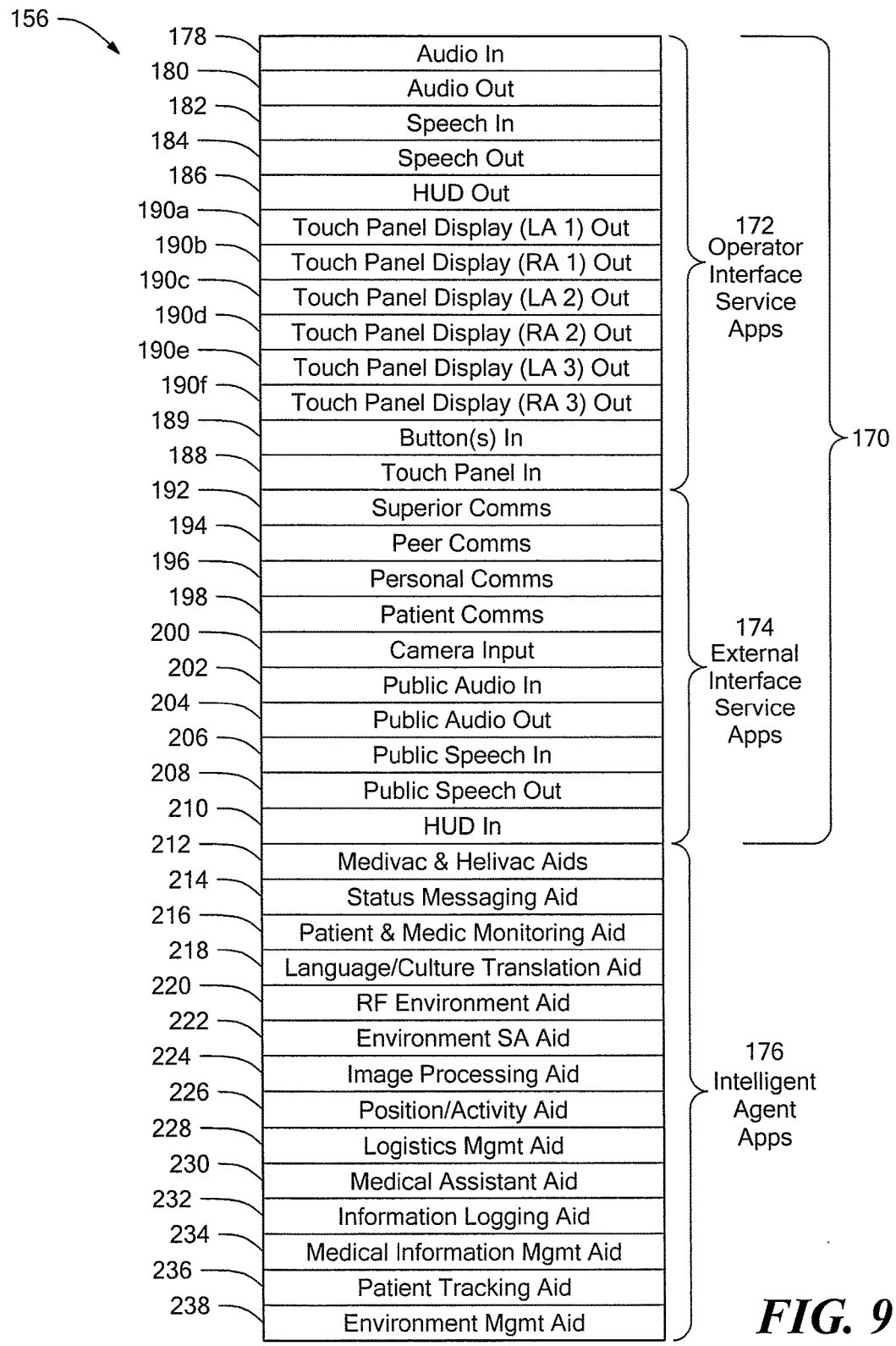
FIG. 9 illustrates an exemplary set of applications supported by the architecture of the arm-wearable intelligent associates shown in FIG. 8.

Referring to FIG. 9, in one exemplary embodiment, the applications 156 (from FIG. 8) include interface service applications 170, both operator interface service applications 172 and external interface service applications 174, and intelligent agent applications 176. The types of operator interface service applications 172 that can be provided include: audio input 178, audio output 180, speech input 182, speech output 184, HUD output 186, touch panel input 188, button(s) input 189, and touch panel display outputs 190a-190f. The external interface service applications 174 may include service applications for: superior communications 192 (link processing with superior nodes, e.g., status, caching, command structure, participants), peer communications 194 (link processing with peer nodes, e.g., status, prioritization schemas, peer lists, connectivity maps, patient lists), personal communications 196 (link processing for personal area network nodes, e.g., component list and capabilities, status, modes), patient communications 198 (link processing for patient nodes, e.g., patient lists, connectivity maps, status, patient data, prioritization schemas), camera input 200, public audio input 202 and output 204, public speech input 206/public speech output 208 and HUD input 210.

The intelligent agent applications 176 can include, for example, Medivac and Helivac aids 212 (e.g., asset request generation and status, asset status and position, send-ahead data (patient condition, etc.), destination information), status messaging aid 214 (e.g., periodic position, state changes), patient and medic monitoring aid 216 (e.g., wireless "smart tag" management and sensor processing, graphic and read-out information, alerts/trends, snapshots for patient record and messaging, sensor integrity, multiple patient support, patient information collation for patient data structures, medic vital signs monitoring and status), language and cultural translation aid 218 (e.g., audio and speech recognition, audio and speech generation, language translation, culture cues, audio clip capture), RF environment aid 220 (e.g., area radio jamming capability, RF environment spectrum use, signal proximity measurement), and environment situational awareness aid 222 (e.g., GPS and motion information, medic location, patient location tagging, medic activity sensing, area SA management, SA reach back management). The intelligent agent applications 176 can further include, for example, image processing aid 224 (e.g., to support image snapshots from available sensors, patient situation information—with send ahead, video clip capture), position/activity aid 226, logistics management aid 228 (e.g., materiel use, running inventory, triggered alerts, resupply point aid), medical assistant aid 230 (e.g., triage support, assessment support, treatment planning, status monitoring), information logging aid 232 (e.g., activity/timestamp), medical information management aid 234 (e.g., medical reference information, medical histories—resident for known group, reachback for new people), patient tracking aid 236 (e.g., patient tagging and configuration, information management, completeness assessment) and environmental management aid 238 (e.g., temperature, humidity, chemical/biological hazard sensing).

Other applications can also be included. For example, an application can be provided to manage lighting based on light sensors inputs. Additional situational awareness aids can provide medical situational awareness in theater, providing commanders and their staffs actionable knowledge and enhanced medical situational awareness for critical decision making. Thus, the system can empower commanders and medics alike with actionable knowledge.

Each IA 122 in a given medic's PAN need not include all of the features in the illustrated IA architecture of FIGS. 8-9, that is, each IA may include all or a subset of the features.

Each IA could include the same subset or a different subset, that is, a different combination of features. Some features could be common to each IA, for redundancy and other purposes, while other features may be unique to a particular IA. Moreover, there may be features not represented in FIGS. 8-9 that could be included as well. There could be variability among the actual software applications as well. In this manner, the IAs could be tailored to specific purposes.

The IA 122 also allows for selectability of functions due to need. For example, for EMTs that aren't in areas with high percentages of foreign language speaking people, the EMTs may not need to have the translation function permanently part of their system. It could be "downloaded" on demand. A combat medic who is "in-country" preferably has a local foreign language installed on his system from the "get-go". The architecture described herein allows for this type of flexibility and modularity both at the node level and for each node's functions.

Figure 10:
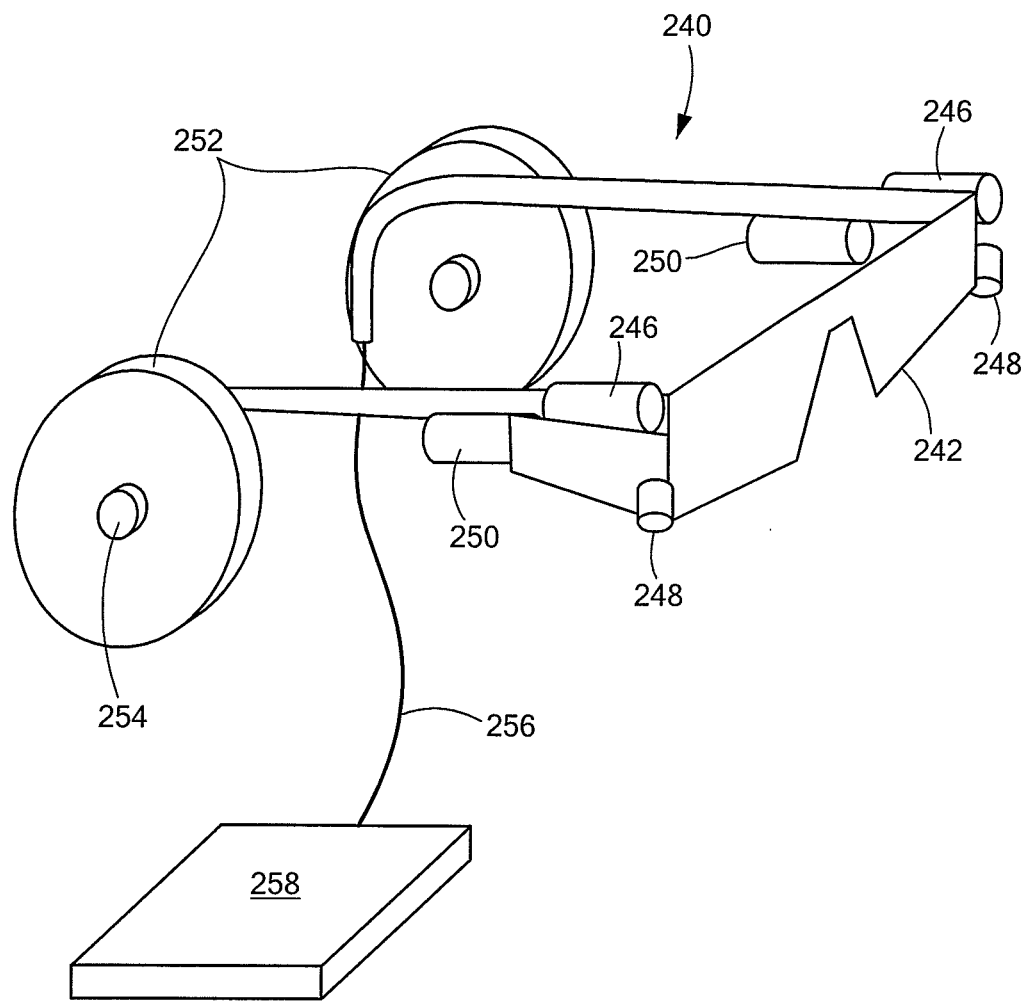
FIG. 10 illustrates an exemplary headset assembly for use in a PAN like that shown in FIG. 3.

Referring now to FIG. 10, an exemplary embodiment of the headset assembly 20b (from FIG. 3), shown here as headset assembly 240, is depicted. The headset assembly 240 includes eyewear 242. Coupled to the eyewear 242 are cameras 246, microphone pick-ups 248, head-up display (HUD) 250 and headphones 252 with earphone/microphone pickup 254 (one on each headphone). Also part of the assembly 240 and coupled to the various other components of the assembly via connection/wire 256 is a headset assembly processor device 258 to perform processing tasks required for operation.

Figure 11:
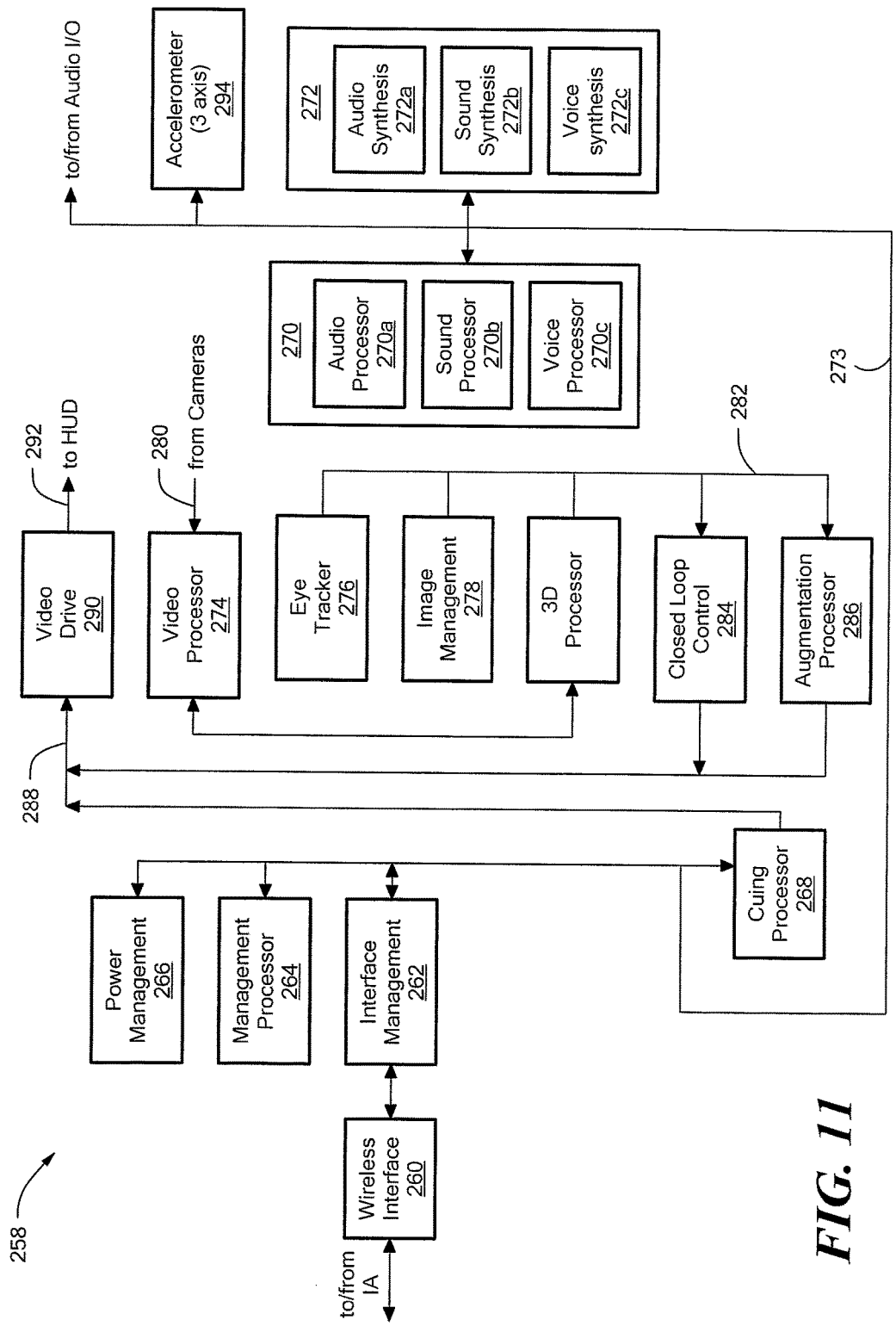
FIG. 11 illustrates an exemplary architecture of a processor device for use in the headset assembly of FIG. 10.

FIG. 11 shows a simplified functional block diagram of the headset assembly processor device 258. The headset assembly processor device 258 includes the following functionality: a wireless interface 260 for transmitting data to and receiving data from PAN device(s) such as intelligent associate 122 (from FIGS. 7-9); interface (IF) management 262; management processor 264; power management 266; and cueing processor 268. Blocks 262, 264 and 268 process information received via the wireless interface 260. Also included are audio, sound and voice processors 270a-270c (collectively, 270) and audio, sound and voice synthesis 272a-272c (collectively, 272) to support audio I/O (for external earphones and microphones). These internal devices are coupled to an internal bus 273. The headset assembly processor device 258 further includes a video processor 274 which, along with an eye tracker 276, image management 278 and 3D processor 279, process input 280 received from the external cameras (cameras 246 from FIG. 10). That result 282 is provided to a closed loop controller 284 and an augmentation processor 286, which provide input 288 (along with the cueing processor 268) to a video drive block 290. The video drive block's output, output 292, is provided to the external HUD (HUD 250 from FIG. 10). The headset assembly processor device 258 also includes a 3-axis accelerometer 294, which is also coupled to internal bus 273. The accelerometer 294, in conjunction with the eye tracker 276, provides orientation and motion information that is processed to understand what is being looked at the headset level. The accelerometer information is also processed at the PAN system level (e.g., via one of the IAs 122) to provide more efficient power management of displays and is coupled with overall mode control.

Figure 12:
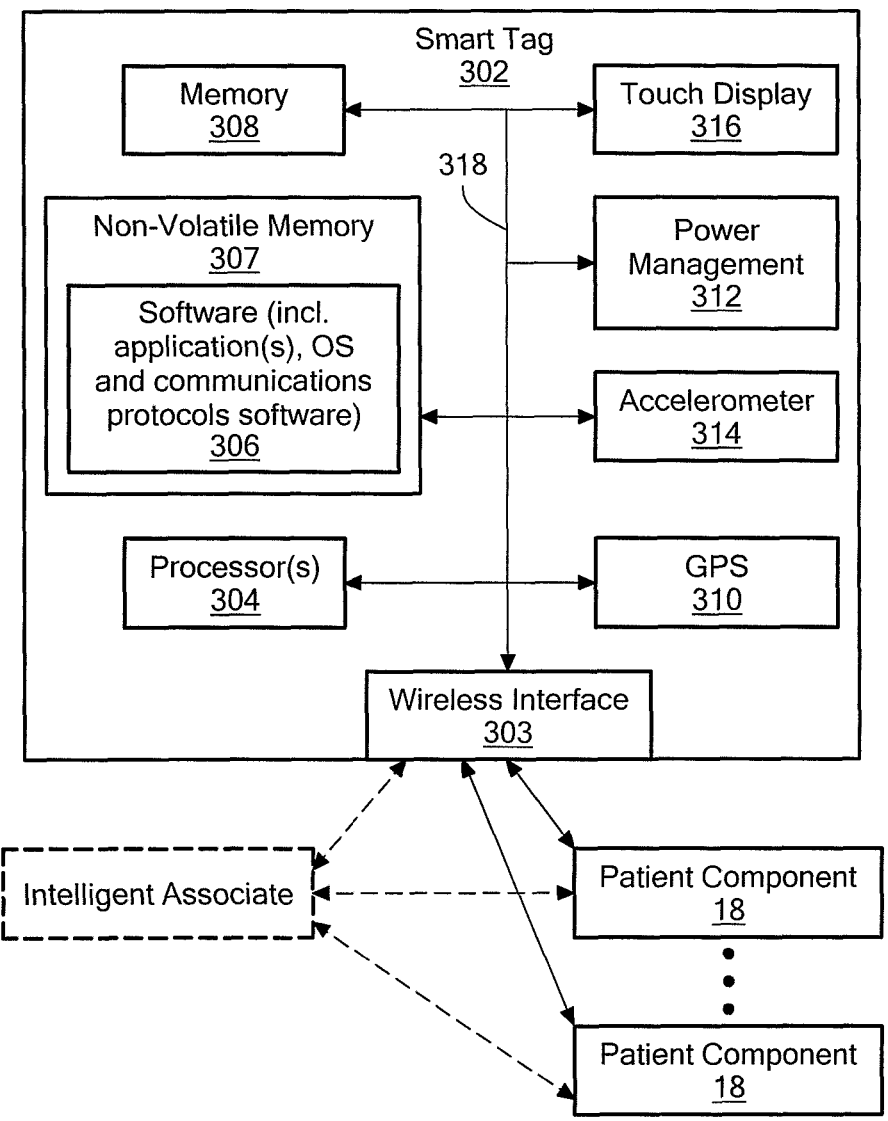
FIG. 12 illustrates an exemplary patient PAN formed by patient components including a smart tag device.

FIG. 12 shows an example of another type of PAN, a patient PAN 300, supported by the architecture of system 12. This network can also be viewed as a special case of the patient network in which a medic component is not a participant. Therefore, the patient PAN 300 includes only patient components 18 as its nodes. They include a smart tag (smart tag 18e from FIG. 2) shown here in an exemplary implementation as smart tag 302. The patient PAN's nodes include one or more other patient components, shown generically as patient components 18.

The figure provides a more detailed (but still simplified) architectural view of the smart tag 302. In this example smart tag architecture, the smart tag 302 includes the following functionality: wireless interface 303; processor(s) 304; software 306 (including applications and other software such as OS and communications protocols software to support patient network communications); nonvolatile memory 307 to store the software 306; and memory 308 (e.g., volatile memory). The software 306 would be copied to the volatile memory 308 (or internal processor memory) for subsequent execution by the processor 304. The smart tag 302 also includes: a GPS 310 for location detection; a power management block 312; an accelerometer 314 for movement detection; and a touch display 316. The various functional blocks of the smart tag 302 are coupled to an interconnect 318 (again, just a simplified depiction of an internal bus architecture).

In the illustrated embodiment, the wireless interface 303 is configured to provide connectivity to another patient component on the same patient. Thus, and as shown, smart tag 302 connects to patients 18 via connections 318. The patient components of the patient PAN, here smart tag 302 and patient components 18, may be participating in a patient network as well (potential patient network interactions are indicated in dash lines). In one embodiment, the smart tag 302 may be the only patient component in communication with IA of a patient network. The smart tag 302 can collect data from the other patient components, for example, sensors, and provide that data to the IA, as was discussed earlier. The smart tag 302 could also be configured with a mode for interacting with intelligent stretchers. FIG. 12 is intended to show only one example of the type of patient PAN that could be formed. Other types of patient components, if provided with enough intelligence and the appropriate wireless interface may connect to other patient components to form a patient PAN in a similar manner.

The nature of the interactions between components in the various networks, including patient, PAN, peer and command networks, is determined by the protocols being utilized by those networks and components. For example, the interactions may be based on a master/slave relationship such as that specified in the Bluetooth standard, or other types of interactions, such as point-to-point or broadcast, to give but a few examples. The sovereignty based architecture discussed above (with reference to FIG. 5) could allow negotiations to determine the appropriate mechanism for connectivity. As an example, Bluetooth requires a master with several slaves that operate on separate frequencies, chosen at the time the master interrogates them. Using Bluetooth as a connection mechanism inherits this protocol, but higher levels could negotiate their response to queries so that an initial sensor patch would be set up initially to respond to the medic's intelligent agent but then be reconfigured to respond to the patient's "smart tag" when coupled to the patient, at which time the information of the sensor patch would be reported to the medic via the "smart tag" interface with the medic.

Preferably, various components of the system 12 are designed to withstand use in harsh operating environments. For example, they may be resistant to temperature changes and extremes. They may also be waterproof, sand proof, smoke proof and shock proof. Furthermore, portions of the system coupled to the medic are provided as having a minimum weight and utilizing minimum power. Power consumption is minimized through the application of intelligent power management techniques, which can minimize information variance. Recharging may occur through various energy harvesting techniques such as when a medic moves his arms, thereby extending mission operations. The system components may be easily field cleaned and sterilized, which has added benefit in a medical community that must be concerned with potential for infections and biohazards. Lastly, the system components are modular and can easily accept field updates.

The architecture described above, which utilizes medical telemetry to augment both the medic 14 and the patient 16, thus provides a human-centered, symbiotic, assistive solution for edge system users. The edge user system 12 may be further understood by considering the following scenarios.

A medic is traveling with his group. As he moves, his "medic system", i.e., the medic component's of the medic's PAN, is tracking his location and providing indications of potential medical "safe-places" and hazards. His medic system reaches back, when connectivity allows, querying and downloading regionally significant information from both tactical and medical data repositories (i.e., the system 12 performs a data mining operation). His equipment is also tracking the health sensors his group is wearing as well as his own sensors. Other sensors measure general environmental conditions. Reach back to environmental data bases for relevant information provides predictive data as well. As conditions change and thresholds are crossed, indications are provided to the medic on the group's health.

A medic comes upon an injured person. When he bends down and begins examining the injured person, he places a sensor patch on the skin, and with a prompt to his medic system, gets immediate data on the injured person's vital signs, e.g., pulse, temperature, respiration, blood pressure, oxygen content, and so forth. Other sensors on the medic's system sniff for chemical and other hazardous materials in the vicinity. Cues off to the side of his vision alert him when critical thresholds are crossed. Looking at other displays located on his arms or via his HUD system, the medic sees detailed data and suggestions regarding the alerts. With simple verbal cues, the medic transitions through multiple simultaneous alerts and guides further processing and prioritization of activities. Other alerts call his attention to displays on his arms where he sees cues on types of problems to look for. Other alerts tell him that information is being requested or is available via reach-back from headquarters to aid in his job. His audio communications system allows him to talk with the rest of the patrol and to annotate an automatically generated patient information folder that will both be sent ahead of the patient and sent with the patient. The medic "tags" the patient with a smart tag that continues to gather data, provide local processing of the signals and effectors uniquely identified with that patient and captures data and command updates from the medic's system. This is done even while the medic moves on to interact with other injured people. The medic's displays, with simple verbal cues, reflect his role and allows him to transition from monitoring multiple patients to diving down to individuals for further annotation with voice, video, recorded sensor information, time/date, and GPS coordinates. The medic views and adds to an automatically generated ongoing log of activities that has been compiled while the medic was busy with other activities and roles. The medic monitors and manages automatically generated ongoing status messaging back to higher tactical and medical chains of command as well as performs creation with auto-population of messages for will calls for medical transport and other messages.

As a medic is working on a patient, another medic from a patrol close by comes over to help. The second medic's system is synchronized with the first medic's system and starts reading the historical and current information from the patient sensors he is in range of and/or the first medic is in range of. His cueing reflects the patient he is near and focusing on while his system monitors others and cues him on priority shifts as patient conditions change.

One of a medic's patients is foreign and speaking a local dialect. The medic's system "hears" the patient, and with verbal authorization by the medic, is provided a translation of what is being said for the medic to read and/or hear in his own language. The medic is provided some key cultural cues and guidance as well. The medic responds verbally, the medics system translates the message into the patient's language and provides it in the media the medic identifies (verbal, text).

One of a medic's patients is a child, duly noted verbally by the medic as he begins examining and treating the patient. As the medic looks down at his wrists, he sees cues, guidance, and reference data for treatment procedures appropriate for children based on his assessment information and reachback to higher command data repositories.

As a medic treats various people, the medic is provided status update on remaining capabilities and assets. At the same time, material and logistic request messages are automatically composed, updated, and, as trigger levels are reached, sent up through the chain of command.

The system 12 exploits technology augmentation to reduce the "Golden Hour" impact for patient damage mitigation by allowing a medic to function as a networked active service. The medic can provide/perform a number of functions including but not limited to: associative information management; active information support from health assessment through first aid conditions; intelligent reach-back; proactive push of information up chains of command and support; on-demand push of sensor/information management to the patient level; peer and group situation awareness sharing; and integration of knowledge, resource application/management, capabilities/status, projection/prediction and augmentation for the hands-on edge user role. By application of an intelligence-based associative architecture in concert with combinations of artificial intelligence, telemetry embedded with the edge user, adaptive and dynamic and social networked communications, modular and redundant capabilities that can be mixed and matched, and multi-modal/multi-media human machine interfaces, a user has infrastructure that can shadow activities and events, interact symbiotically with the user, perform mundane information tasks, anticipate/monitor information needs of a situation and more effectively manage the total information to and from the user. Also, the system is based on a general construct naturally extendable to, and interactive with, other operational domains.

All references cited herein are hereby incorporated herein by reference in their entirety.

Having described preferred embodiments which serve to illustrate various concepts, structures and techniques which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

What is claimed is:

1. A system for medics to collect information from one or more patients, the system comprising:
   one or more sensors coupled to a first patient, wherein the first patient sensors automatically collect patient information for the first patient;
   one or more sensors coupled to a second patient, wherein the second patient sensors automatically collect patient information for the second patient;
   a first personal area network (PAN) coupled to a first medic;
   a second PAN coupled to a second medic, wherein the first and second PANs each include a plurality of components as nodes,
   wherein the system is configured to, in response to the first medic approaching the first patient:
      automatically establish a connection between the first PAN and the first patient sensors;
      automatically transfer, to the first PAN, first patient information collected by the first patient sensors since a previous connection was established between the first PAN and the first patient sensors; and
      store the first patient information within the first PAN;
   wherein the system is configured to, in response to the first medic moving away from the first patient and approaching the second patient:
      automatically drop the connection between the first PAN and the first patient sensors;
      automatically establish a connection between the first PAN and the second patient sensors;
      automatically transfer, to the first PAN, second patient information collected by the second patient sensor since a previous connection was established between the first PAN and the second patient sensors; and
      store the second patient information within the first PAN; and
   wherein the system is configured to, in response to the first medic approaching the second medic:
      automatically establish a peer network between the first PAN and the second PAN; and
      automatically transmit the patient information stored in the first PAN to the second PAN.

2. The system of claim 1 further comprising:
   a communications adapter configured to establish communications with each of the first and second PANs through a third wireless network; and
   wherein the communications adapter is further configured to connect to a legacy infrastructure and provide for flow of information between each of the first and second PANs and the legacy infrastructure.

3. The system of claim 2 wherein at least one of the first PAN components comprises an intelligent associate that is configured to receive information from legacy infrastructure via the communications adapter.

4. The system of claim 3 wherein at least one of the first PAN components comprises an intelligent associate that is configured to receive data mining information from the legacy infrastructure via communication adapter.

5. The system of claim 2 wherein the one or more first patient sensors include a device configured to capture physiological information through contact with the first patient and transmit that physiological information to at least one component of the first and second PANs.

6. The system of claim 5 wherein the one or more first patient sensors further include a smart tag coupled to the first patient.

7. The system of claim 1 wherein when the first medic approaches the first patient, each first patient sensor and at least one component of the first PAN automatically sense each other and begin information exchanges via a first wireless network based upon communications range capabilities.

8. The system of claim 7 wherein a connection is formed between each first patient sensor and at least one component of the first PAN based on the information exchanges.

9. The system of claim 8 wherein the information exchanges comprise a mutual negotiation according to communication protocols supported by the system.

10. The system of claim 8 wherein, in response to the first medic moving away from the first patient toward the second patient, at least one component of the first PAN automatically disconnects from each of the first patient sensors based upon the communications range capabilities.

11. The system of claim 8 wherein as the medic moves away from the first patient toward the second patient one or more ad-hoc networks are formed.

12. The system of claim 1 wherein at least one of the first PAN components comprises an arm-worn intelligent associate.

13. The system of claim 1 wherein the first PAN components comprises two arm-worn intelligent associates and wherein one arm-worn intelligent associate is configured to interact with at least one first patient sensors and the other arm-worn intelligent associate is configured to interact with other first PAN components.

14. The system of claim 12 wherein the first PAN components further include a headset assembly.

15. The system of claim 14 wherein the first PAN further includes one or more sensors to monitor the health of the first medic.

16. The system of claim 15 wherein the first PAN further includes environment sensors.

17. A method for medics to collect information from one or more patients, the method comprising:
   coupling one or more sensors to a first patient, wherein the first patient sensors automatically collect patient information for the first patient;
   coupling one or more sensors to a second patient, wherein the second patient sensors automatically collect patient information for the second patient;
   coupling a first personal area network (PAN) to a first medic;
   coupling a second PAN to a second medic, wherein the first and second PANs each include a plurality of components as nodes;
   in response to the first medic approaching the first patient:
      automatically establishing a connection between the first PAN and the first patient sensors;
      automatically transferring, to the first PAN, first patient information collected by the first patient sensors since a previous connection was established between the first PAN and the first patient sensors; and
      storing the first patient information within the first PAN;
   in response to the first medic moving away from the first patient and approaching the second patient:
      automatically dropping the connection between the first PAN and the first patient sensors;
      automatically establishing a connection between the first PAN and the second patient sensors;
      automatically transferring, to the first PAN, second patient information collected by the second patient sensor since a previous connection was established between the first PAN and the second patient sensors; and storing the second patient information within the first PAN; and in response to the first medic approaching the second medic:

automatically establishing a peer network between the first PAN and the second PAN; and automatically transmitting the patient information stored in the first PAN to the second PAN.

18. The method of claim 17 wherein the one or more first patient sensors include a device configured to capture physiological information through contact with the first patient and transmit that physiological information to at least one component of the first and second PANs.

19. The method of claim 18 wherein the one or more first patient sensors further include a smart tag to maintain an electronic patient record for the first patient to whom the smart tag has been coupled, the smart tag being configured to provide and receive information updates for the electronic patient record when the smart tag is in communication with at least one component of the first and second PANs.

* * * * *